(12) United States Patent
Khire et al.

(10) Patent No.: US 9,034,861 B2
(45) Date of Patent: May 19, 2015

(54) MEK INHIBITORS USEFUL IN THE TREATMENT OF DISEASES

(75) Inventors: Uday R. Khire, Orange, CT (US); Mahendra Devichand Chordia, Charlottesville, VA (US)

(73) Assignee: Allomek Therapeutics LLC, Farmington, CT (US)

( * ) Notice: Subject to any disclaimer, the term of this patent is extended or adjusted under 35 U.S.C. 154(b) by 508 days.

(21) Appl. No.: 13/501,442

(22) PCT Filed: Oct. 13, 2010

(86) PCT No.: PCT/US2010/052514
§ 371 (c)(1),
(2), (4) Date: Apr. 11, 2012

(87) PCT Pub. No.: WO2011/047055
PCT Pub. Date: Apr. 21, 2011

(65) Prior Publication Data
US 2012/0208859 A1      Aug. 16, 2012

Related U.S. Application Data

(60) Provisional application No. 61/250,936, filed on Oct. 13, 2009.

(51) Int. Cl.
*C07D 291/02* (2006.01)
*C07D 291/08* (2006.01)

(52) U.S. Cl.
CPC .................................... *C07D 291/08* (2013.01)

(58) Field of Classification Search
None
See application file for complete search history.

(56) References Cited

U.S. PATENT DOCUMENTS

| | | | |
|---|---|---|---|
| 5,861,510 A | 1/1999 | Piscopio et al. | |
| 5,863,949 A | 1/1999 | Robinson et al. | |
| 6,891,066 B2 | 5/2005 | Rewcastle et al. | |
| 7,078,438 B2 | 7/2006 | Rewcastle et al. | |
| 7,652,047 B2 | 1/2010 | Abdellaoui et al. | |
| 7,759,518 B2 | 7/2010 | Maderna et al. | |
| 7,820,664 B2 | 10/2010 | Vernier et al. | |
| 7,842,836 B2 | 11/2010 | Yan et al. | |
| 7,897,624 B2 | 3/2011 | Yan et al. | |
| 8,044,240 B2 | 10/2011 | Dimock | |
| 8,101,799 B2 | 1/2012 | Maderna et al. | |
| 8,187,635 B2 | 5/2012 | Karavas et al. | |
| 2009/0233915 A1 | 9/2009 | Isshiki et al. | |
| 2010/0197676 A1 | 8/2010 | Isshiki et al. | |
| 2011/0033539 A1 | 2/2011 | Quart et al. | |
| 2011/0060049 A1 | 3/2011 | Vernier et al. | |

FOREIGN PATENT DOCUMENTS

| CN | 101124199 B | 2/2008 |
|---|---|---|
| CN | 101495118 B | 7/2009 |
| EP | 0606046 A1 | 7/1994 |
| EP | 780386 A1 | 6/1997 |
| EP | 0818442 A2 | 1/1998 |
| EP | 931788 A2 | 7/1999 |
| EP | 1004578 A2 | 5/2000 |
| WO | WO 90/05719 A1 | 5/1990 |
| WO | WO 96/27583 A1 | 9/1996 |
| WO | WO 96/33172 A1 | 10/1996 |
| WO | WO 98/03516 A1 | 1/1998 |

(Continued)

OTHER PUBLICATIONS

Pearson et al., "Mitogen-Activated Protein (MAP) Kinase Pathways: Regulation and Physiological Functions," Endocr. Rev., 2001, 153-183.
Sebolt and Herrara, "Targeting the mitogen-activated protein kinase cascade to treat cancer," Nature Rev. Can., 2004, 937-947.
Fremin and Meloche, "From basic research to clinical development of MEK1/2 inhibitors for cancer therapy," J. Hemato & Onco., 2010, 3-8.
Iverson et al., "RDEA119/BAY 869766: A Potent, Selective, Allosteric Inhibitor or MEK1/2 for the Treatment of Cancer," Can. Res., 2009, 69 (17) 6839-6847.

(Continued)

*Primary Examiner* — Noble Jarrell
(74) *Attorney, Agent, or Firm* — David W. Ladner; Ladner Patent Management LLC

(57) ABSTRACT

The invention pertains to compound of Formula (I) wherein X, Y, Z, $R^1$, $R^2$, $R^3$, $R^4$, A and A' are as described hereinabove. Formula (I) and (II) compounds can be used in pharmaceutical compositions, useful for the treatment of diseases.

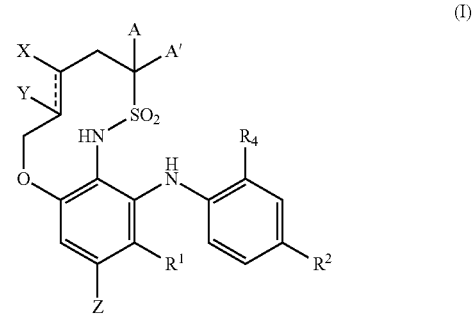

(I)

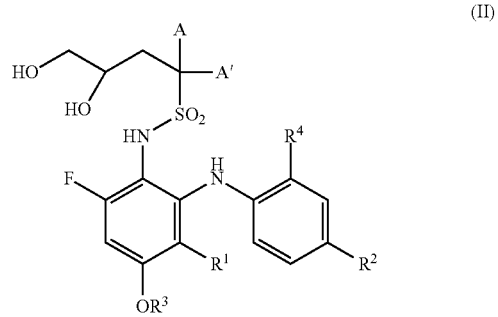

(II)

10 Claims, No Drawings

(56) References Cited

FOREIGN PATENT DOCUMENTS

| WO | WO 98/07697 A1 | 2/1998 |
|---|---|---|
| WO | WO 98/30566 A1 | 7/1998 |
| WO | WO 98/33768 A1 | 8/1998 |
| WO | WO 98/34915 A1 | 8/1998 |
| WO | WO 98/34918 A1 | 8/1998 |
| WO | WO 99/07675 A1 | 2/1999 |
| WO | WO 99/29667 A1 | 6/1999 |
| WO | WO 99/52889 A1 | 10/1999 |
| WO | WO 99/52910 A1 | 10/1999 |
| WO | WO 00/74681 A1 | 12/2000 |
| WO | WO 03/062191 A1 | 7/2003 |
| WO | WO 2007/014011 A2 | 2/2009 |
| WO | WO 2009/018233 A1 | 2/2009 |
| WO | WO 2009/018238 A1 | 2/2009 |
| WO | WO 2009/129246 A2 | 4/2009 |
| WO | WO 2010/145197 A1 | 12/2010 |

OTHER PUBLICATIONS

Montagut and Settleman, "Targeting the RAF-MEK-ERK pathway in cancer therapy," Cancer Lett., 2009, 283 (2) 125-134.

Price, "Putative allosteric MEK1 and MEK2 inhibitors," Expert Opin. Ther. Patents, 2008, 18(6) 603-627.

Saulnier et al., "An efficient method for the synthesis of guanidino prodrugs," Bioorganic and Medicinal Chemistry Letters, 1994, 4 1985.

Ardea Bioscience and Bayer HealthCare Enter into Global Agreement Focused on the Development of MEK Inhibitors for the Treatment of Cancer, Press Release, Apr. 28, 2009.

Yan et al., Design and Synthesis of RDEA119 a Potent and Orally Bioavailable MEK Inhibitor, 2008, Poster # P464, Symposium on Medicinal Chemistry (EFMC ISMC) Aug. 31, 2008 to Sep. 4, 2008, Vienna, Austria.

Wang et al., "Recent Advances of MEK Inhibitors and their Clinical Progress, " Current Topics in Medicinal Chemistry, 2007, 7(14) 1364-1378.

Chordia et al., A Potent MEK Inhibitor, CIP-1374, With Oral Availability and Prolonged Half Life in Mice, Abstract #736, American Associatation of Cancer Research, Apr. 18, 2010, Washington, DC.

Herranz et al., "Osmium-Catalyzed Vicinal Oxyamination of Olefins by N-Chloro-N-metallocarbamates," J. Org. Chem, 1980 45, 2710-2713.

LopezLanger, "New Methods of Drug Delivery ," Science, 1990, 249 1527-1533.

Bai et al., "Highly active phosphine-free carbene ruthenium catalyst for cross-metathesis of acrylonitrile with functionalized olefins," Tetrahedron Letters 2005, 46 7225-7228.

Treat et al., "Liposome encapsulated doxorubicin preliminary results of Phase I and Phase I trials," in "Liposomes in the therapy of infectious diseases and cancer," Lopez-Berestein et al., Eds., Liss, NY, 1989, pp. 353-365.

PCT/US2010/052514 Search Report Dated Apr. 17, 2012.

Mackeigan et al., MEK Inhibition Enhances Paclitaxel-Induced Tumor Apoptosis, J. Biol. Chem., 2000, 275:38953-38956. (USA).

Zhang et al., Study of MEK2/ERK Signal transduction pathway in the colorectal cancer, Chinese Journal of General Surgery, 13 (4). 257-260, Apr. 30, 2004, (China).

Friday et al, Advances in Targeting teh Ras/Raf/MEK/Erk Mitogen-Activated Protein Kinase Cascade with MEK Inhibitors for Cancer Therapy, Clinical Cancer Research, 2008; 14:342-346. (USA).

English Translation of CN201080053278.5, The State Intellectual Property Office of the People's Republic of China, Search Report, Original Document Dated Oct. 31, 2013; English Translation Dated Nov. 29, 2013.

MEK INHIBITORS USEFUL IN THE TREATMENT OF DISEASES

CROSS REFERENCE TO RELATED APPLICATION

The present application claims the benefit of U.S. provisional application No. 61/250,936, filed on Oct. 13, 2009.

FIELD OF THE INVENTION

The invention relates to novel inhibitors of the mitogen-activated protein (MAP) kinases, specifically the MEK1 and MEK2, and the treatment of disease states associated with such inhibition through the effects of inhibiting the RAF/MEK/ERK pathway.

BACKGROUND OF THE INVENTION

Mitogen-activated protein kinase (MAPK) is relevant to many cancers. MAPKs specifically phosphorylate serine/threonine residues of proteins, that are activated by a variety of external stimuli (for example, mitogens and growth factors) to manifest its actions inside the cell. The activation of MAPKs regulates many functions of the cells with physiological implications such as cell growth, survival, apoptosis, differentiation, proliferation and gene expression. (1)

MEK 1 and 2 are two human kinases in the middle of the classical MAPK-cascade involving upstream RAS-RAF and downstream ERKs. This signal transduction cascade resulting in phosphorylation of ERKs is extensively studied in cancer pathology. The phosphorylated-ERK upon its translocation to nucleus activates several transcription factors to induce the expression of many genes required for cell survival and proliferation. (2) Because of the very high selectivity conferred on MEKs to phosphorylate only ERK1 and ERK2, targeting its inhibition offers an attractive strategy for anticancer drug discovery. (3)

In addition, the mechanism of action of the known MEK inhibitors such as PD98059 and U0126 is non ATP-competitive (binding to allosteric site) and thus may have least side effects in clinics. Few of the MEK inhibitors currently undergoing clinical studies, (4,5). include AZD-6244, (Array Biopharma, Astra Zeneca), RDEA-119 (Ardea Biosciences, Bayer, see A. Maderna et al, U.S. Pat. No. 7,759,518), in combination with sorafenib, displaying a significant response in sorafenib resistant hepatoma cells, and XL-518 (Exelixis) for solid tumors.

Identification of inhibitors of mitogen-activated protein (MAP) protein kinases, especially MEK1 and/or MEK2 inhibitors, is a widely active area in pharmaceutical research because of the potential use of such inhibitors as drugs to treat a variety of disease states affected by such inhibition. Comprehensive reviews of the state of the art in this field is found in S. Price, Expert Opin. Ther. Patents (2008) 18 (6), 603-627 and C. Fremin, S. Meloche, Journal of Hematology and Oncology 2010, 3:8.

Despite current progress in MEK inhibitor research, it would nevertheless be highly beneficial to discover additional MEK inhibitors with improved pharmacological properties such as potency, oral bioavailability, half-life, and low CNS penetration for the treatment of various types of cancer. Compounds with such properties lead to more efficacious treatments of cancers, while minimizing undesirable side effects.

Furthermore, in additional to their potential as anti-tumor agents, MEK inhibitors are described in the art as having potential use for the treatment of anti-inflammatory diseases, chronic obstructive pulmonary disease, cardio-facio-cutaneous syndrome, and influenza. Well over 50 patent families exist which describe various compounds purported to have MEK activity.

REFERENCES

1. G. Pearson, et al., *Endocr. Rev.*, 2001, 153-183.
2. J. S. Sebolt and R. Herrera, *Nature Rev. Can.* 2004, 937-947.
3. C. Fremin and S. Meloche, *J. Hemato & onco.*, 2010, 3-8.
4. C. Iverson, et al. *Can. Res.*, 2009, 6839-6847.
5. C. Montagut and J. Settleman, *Cancer Lett*, 2009, 125-134

SUMMARY OF THE INVENTION

The invention is directed to a compound of Formula (I):

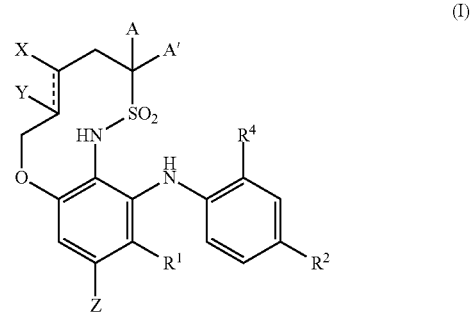

(I)

wherein
  $R^1$ is H or F;
  $R^2$ is Br or I;
  $R^4$ is H, F, Cl, or Br;
  ═══ represents a double or single bond;
  X and Y are independently selected from
    H,
    OH,
    $OR^3$, or
    $NH_2$,
    provided that when ═══ represents a double bond, X and Y are H;
  Z is H, F, or $OR^3$;
    wherein $R^3$ is $C_1$-$C_6$ alkyl;
  A and A' are independently H, or $C_1$-$C_6$alkyl;
  or
  A and A', together with the C atom to which they are attached, form a cyclopropyl, cyclobutyl or cyclopentyl ring;
or a pharmaceutically acceptable salt, solvate or tautomer thereof.

In addition, the invention is directed to a compound of Formula (II)

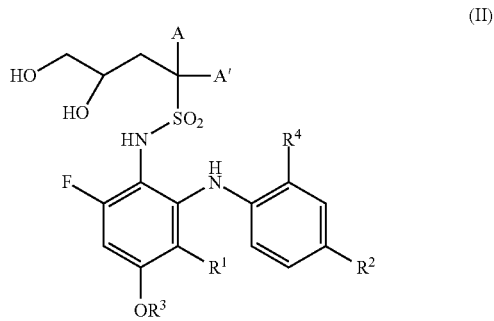

(II)

wherein
- $R^1$ is H or F;
- $R^2$ is Br or I;
- $R^3$ is $C_1$-$C_6$ alky;
- $R^4$ is H, F, Cl, or Br;

and

A and A' are independently H, or $C_1$-$C_6$alkyl;

or

A and A', together with the C atom to which they are attached, form a cyclopropyl, cyclobutyl or cyclopentyl ring;

or a pharmaceutically acceptable salt, solvate or tautomer thereof.

The compounds of Formula (I) and (II) are inhibitors of the MEK enzyme, a biological activity useful for the treatment of diseases in which such inhibition is advantageous. These diseases include, but are not limited to hyperproliferative disorders, cancer, inflammation, arthritis and COPD.

The invention is also directed to a method of treating a hyperproliferative disorder in a mammal, including a human, comprising administering to said mammal a therapeutically effective amount of the compound of Formula (I) or Formula (II) or a pharmaceutically acceptable salt, solvate, or tautomer thereof.

This invention is also directed to a method of treating an inflammatory disease, condition or disorder in a mammal, including a human, comprising administering to said mammal a therapeutically effective amount of the compound of Formulae (I)-(II), or a pharmaceutically acceptable salt, solvate, or tautomer thereof.

The invention is also directed to a method of treating a disorder or condition which is modulated by the MEK cascade in a mammal, including a human, comprising administering to said mammal an amount of the compound of Formula (I) or Formula (II), or a pharmaceutically acceptable salt, solvate, hydrate or derivative thereof, effective to modulate said cascade. The appropriate dosage for a particular patient can be determined, according to known methods, by those skilled in the art.

This invention is also directed to pharmaceutical compositions comprising effective amounts of a compound of Formula (I) or Formula (II) or a pharmaceutically acceptable salt, solvate, or tautomer thereof. In some embodiments, the pharmaceutical compositions further comprise a pharmaceutically acceptable carrier. Such compositions may contain adjuvants, excipients, preservatives, agents for delaying absorptions, fillers, binders, adsorbents, buffers, disintegrating agents, soulblizing agents, other carriers and other inert ingredients. Methods of formulation of such compositions are well known in the art.

In addition to anti-proliferative activity, the compounds of the invention display advantageous pharmacological properties, such as high oral bioavailability, longer half-life and with low brain barrier penetration. Such properties are desirable for pharmaceuticals because they are associated with medicaments that are more efficacious and have fewer side effects.

DETAILED DESCRIPTION OF THE INVENTION

The terms identified above have the following meaning throughout:

The term "optionally substituted" means that the moiety so modified may have from none to up to at least the highest number of substituents possible. The substituent may replace any H atom on the moiety so modified as long as the replacement is chemically possible and chemically stable. When there are two or more substituents on any moiety, each substituent is chosen independently of any other substituent and can, accordingly, be the same or different.

The term "halo" means an atom selected from Cl, Br, F, and I.

The term "pharmaceutically acceptable salt" refers to a relatively non-toxic, inorganic or organic acid addition salt of a compound of the present invention (see, e.g., Berge et al., *J. Pharm. Sci.* 66:1-19, 1977).

The term "MEK inhibitor" as used herein refers to a compound that exhibits an $IC_{50}$ with respect to MEK activity of no more than about 100 µM or not more than about 50 µM, as measured in the MEK Enzyme inhibitory assay described generally herein. "$IC_{50}$" is that concentration of inhibitor which reduces the activity of an enzyme (e.g., MEK) to half-maximal level. Compounds described herein have been discovered to exhibit inhibition against MEK.

The terms "subject", "patient", or "individual", as used herein in reference to those suffering from a disorder and the like, encompasses mammals and non-mammals. Examples of mammals include, but are not limited to, any member of the Mammalian class: humans, non-human primates such as chimpanzees, and other apes and monkey species, farm animals such as cattle, horses, sheep, goats, swine, domestic animals such as rabbits, dogs, and cats; laboratory animals including rodents, such as rats, mice and guinea pigs and the like. Examples of non-mammals include, but are not limited to, birds, fish and the like. In one embodiment of the methods and compositions provided herein, the mammal is a human.

The terms "treat", "treating", or "treatment", and other grammatical equivalents as used herein, include alleviating, abating or ameliorating a disease or condition symptoms, preventing additional symptoms, ameliorating or preventing the underlying metabolic causes of symptoms, inhibition the disease or condition, e.g., arresting the development of the disease or condition, relieving the disease or condition, causing regression of the disease or condition, reliving a condition caused by the disease or condition or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient a risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being tread. The result can be reduction and/or alleviation of the signs, symptoms, or causes of a disease, or any other desired alteration of a biological system. For example an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer", "administering", "administration", and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton Pa.

A salt of a compound of Formula (I) or Formula (II) may be prepared in situ during the final isolation and purification of a compound or by separately reacting the purified compound in its free base form with a suitable organic or inorganic acid and isolating the salt thus formed. Likewise, when the compound of Formula (I) or Formula (II) contains a carboxylic acid moiety, a salt of said compound of Formula (I) or Formula (II) may be prepared by separately reacting it with a suitable inorganic or organic base and isolating the salt thus formed.

Representative salts of the compounds of Formula (I) include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides; aralkyl halides like benzyl and phenethyl bromides, and the like The term "solvate" refers to either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of the compound as described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general solvated forms are considered equivalent to the unsolvated forms, for the purposes of the compounds and methods provided herein.

The term "ester" refers to a derivative of the compound of Formula (I) or (II) which can be prepared by esterification of one or more hydroxyl functional groups present in the molecule. Esterification methods are well known in the art. These methods include, but are not limited to, allowing the hydroxyl-containing compound of Formula to react with a suitable carboxylic acid in the presence of a catalytic amount of acid such as a mineral acid (e.g. HCl, $H_2SO_4$ and the like), or allowing the hydroxyl containing compound of Formula (I) or (II) to react with a carboxylic acid derivative, e.g. an acid chloride or anhydride, optionally in the presence of a mild base such as pyridine, triethylamine or the like. Such ester derivatives may be pharmaceutically active in their own right, or act as prodrugs to facilitate stability or delivery of the pharmaceutically active moiety in vivo.

The term "tautomer" refers to all isomeric forms of the compound which may exist alone or in equilibrium with each other in solution due to the presence of a tautomeric group or groups in a molecule. Such isomerization is called tautomerization and is the formal migration of a hydrogen atom within a molecule, accompanied by a switch of a single bond and an adjacent double bond. Groups which are tautomeric pairs include, but are not limited to, keto-enol, imine-enamine, lactam-lactim and amide-imidic acid.

The term "prodrug" refers to a drug precursor of a compound of Formula (I) or Formula (II) that, following administration to a subject and subsequent absorption, are converted to an active, or a more active species via some process such as conversion by a metabolic pathway. Some prodrugs have a chemical group present that renders it less pharmaceutically active and/or confers stability or other advantageous property to the molecule such as solubility. One the chemical group has been cleaved and/or modified from the prodrug, the active drug is generated. Prodrugs are often useful because in some situations, they may be easier to administer than the parent drug. They may, for example, be bioavailable by oral administration whereas the parent is not. The prodrug may also have improved solubility in pharmaceutical compositions over the parent drug. Prodrugs and their preparation are well known to those skilled in the art such as described in Saulnier et al., (1994), Bioorganic and Medicinal Chemistry Letters, Vol. 4, p. 1085.

The compounds of Formulae (I)-(II) may contain one or more asymmetric centers, depending upon the location and nature of the various substituents desired. Asymmetric carbon atoms may be present in the (R) or (S) configuration. Preferred isomers are those with the absolute configuration which produces the compound of Formulae (I)-(II) with the more desirable biological activity. In certain instances, asymmetry may also be present due to restricted rotation about a given bond, for example, the central bond adjoining two aromatic rings of the specified compounds.

Substituents on a ring may also be present in either cis or trans form, and a substituent on a double bond may be present in either Z or E form.

When a phenyl ring is substituted with one or more substituents, the substituent(s) may be attached to the phenyl ring at any available C atom. When there is more than one substituent on a phenyl ring, each substituent is selected independently from the other so that they may be the same or different.

It is intended that all isomers (including enantiomers and diastereomers), either by nature of asymmetric centers or by restricted rotation as described above as separated, pure or partially purified isomers or racemic mixtures thereof, be included within the scope of the instant invention. The purification of said isomers and the separation of said isomeric mixtures may be accomplished by standard techniques known in the art.

The particular process to be utilized in the preparation of the compounds of this invention depends upon the specific compound desired. Such factors as the selection of the specific X, Y, Z, A, A', and $R^1$-$R^4$ moieties, and the specific substituents possible at various locations on the molecule, all play a role in the path to be followed in the preparation of the specific compounds of this invention. Those factors are readily recognized by one of ordinary skill in the art.

A first embodiment of the invention is the compound of Formula (Ia)

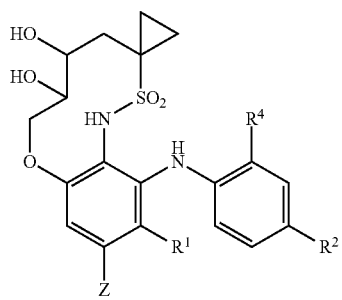

(Ia)

wherein
$R^1$ is H or F;
$R^2$ is Br or I;
$R^4$ is H, F, Cl, or Br;
and
Z is H, F, or MeO;
or a pharmaceutically acceptable salt, solvate, or tautomer thereof.

A second embodiment of the invention is the compound of Formula (Ib)

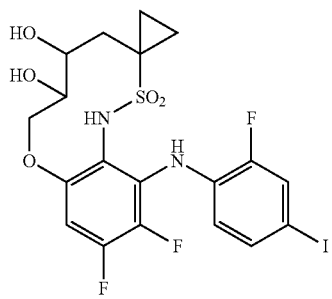

(Ib)

or a pharmaceutically acceptable salt, solvate, or tautomer thereof.

third embodiment of the invention is the compound of Formula (Ic):

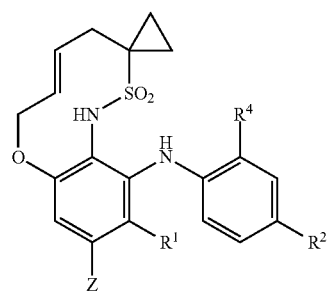

(Ic)

wherein
$R^1$ is H or F;
$R^2$ is Br or I;
$R^4$ is H, F, Cl, or Br;
Z is H, F, or $OR^3$;
wherein $R^3$ is $C_1$-$C_6$ alkyl;
or a pharmaceutically acceptable salt, solvate or tautomer thereof.

A fourth embodiment of the invention is the compound of Formula (Id)

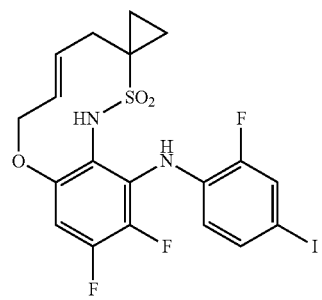

(Id)

or a pharmaceutically acceptable salt, solvate or tautomer thereof.

A fifth embodiment of the invention is the compound of Formula (IIa)

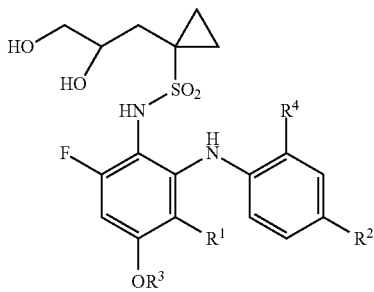

(IIa)

wherein
$R^1$ is H or F;
$R^2$ is Br or I;
$R^3$ is $C_1$-$C_6$ alkyl;
$R^4$ is H, F, Cl, or Br;
or a pharmaceutically acceptable salt, solvate or tautomer thereof.

A sixth embodiment of the invention is the compound of Formula (IIb)

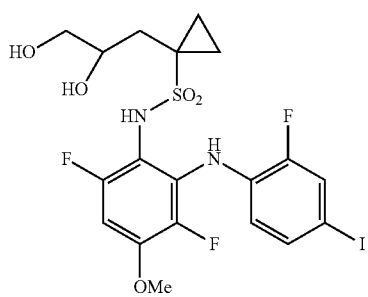

(IIb)

or a pharmaceutically acceptable salt, solvate or tautomer thereof.

Other embodiments of the invention are listed in Table 1 below:

TABLE 1

| Example No. | Compound |
|---|---|
| 1 | *(structure: phenyl-O-CH2-CH=CH-CH2-C(cyclopropyl)(SO2-NH-) linked to difluorophenyl-NH-fluoro-iodophenyl)* |
| 2 | *(structure: similar to 1, with 4-bromo-2-fluoroanilino group)* |
| 3 | *(structure: similar to 1, with 4-iodoanilino group)* |
| 4 | *(structure: similar to 1, with 2-chloro-4-iodoanilino group)* |
| 5 | *(structure: similar to 1, with OMe substituent and 2-fluoro-4-iodoanilino group)* |

TABLE 1-continued

| Example No. | Compound |
|---|---|
| 6 | *(structure: macrocyclic compound with cyclopropyl-SO2-NH, fluoro, 2-fluoro-4-iodoanilino)* |
| 7 | *(structure: macrocyclic compound with cyclopropyl-SO2-NH, difluoro, 2-fluoro-4-iodoanilino)* |
| 8 | *(structure: dihydroxy-butyl-cyclopropyl-SO2-NH, difluoro, 2-fluoro-4-iodoanilino)* |
| 8a (fast eluting isomer on reverse phase HPLC)* | *(structure: same as 8, single isomer)* |
| 8b (slow eluting isomer on reverse phase HPLC)* | *(structure: same as 8, other isomer)* |

TABLE 1-continued
| Example No. | Compound |
|---|---|
| 9 | 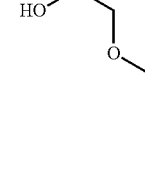 |
| 10 | |
| 11 | |
| 12 | |
| 13 | |
| 14 | 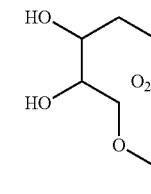 |
| 15 | |
| 16 | |
| 17 | |
| 18a | |

TABLE 1-continued

| Example No. | Compound |
|---|---|
| 18b | |
| 19 | |
| 20a | |
| 20b | |

Preparation of Compounds

The particular process to be utilized in the preparation of the compounds of this invention depends upon the specific compound desired. Such factors as the specific substituents possible at various locations on the molecule, all play a role in the path to be followed in the preparation of the specific compounds of this invention. Those factors are readily recognized by one of ordinary skill in the art.

Sensitive or reactive groups on any of the intermediate compounds may need to be protected and deprotected during any of the above methods for forming esters. Protecting groups in general may be added and removed by conventional methods well known in the art (see, e.g., T. W. Greene and P. G. M. Wuts, Protective Groups in Organic Synthesis; Wiley: New York, 1999).

Compounds of the present invention may be made according to the Reaction Schemes below. In these schemes, unless otherwise noted, the groups X, Y, Z, $R^1$, $R^2$, $R^3$, RA and A' have the same definitions as described above.

A general method for preparation of the compound of Formula (I) is illustrated below in Reaction Scheme 1.

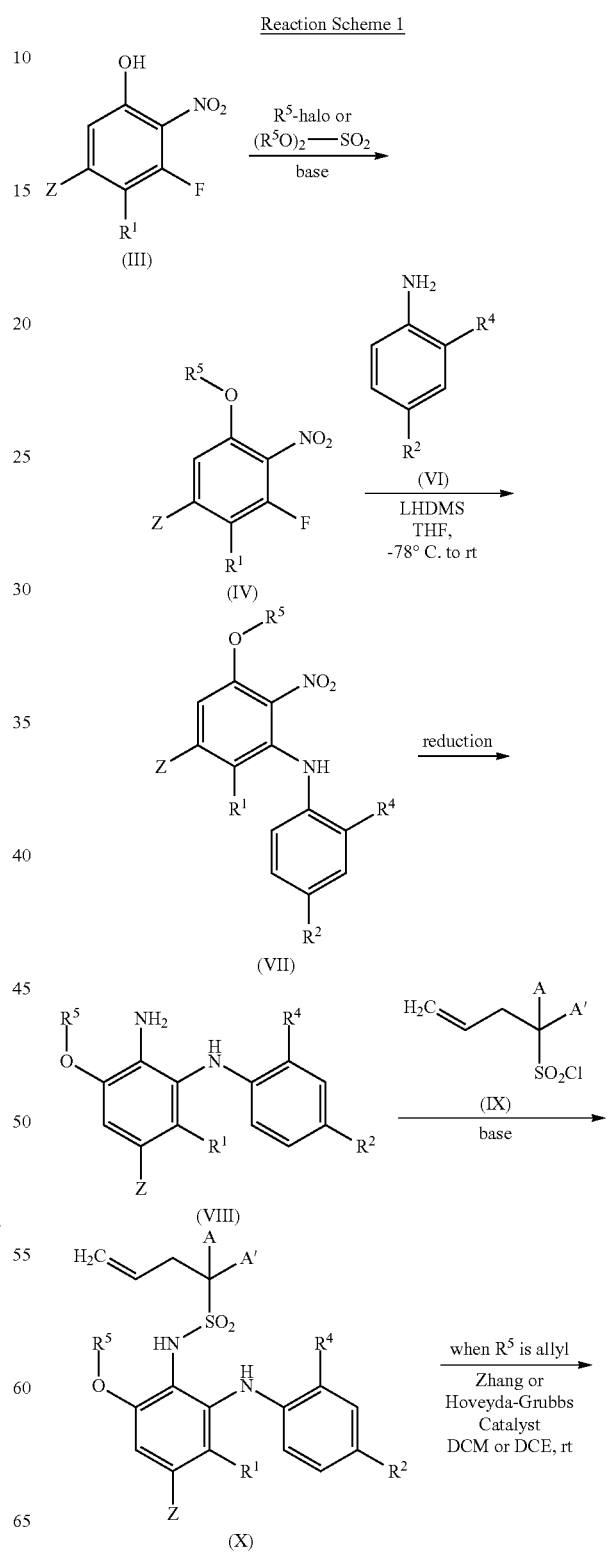

Reaction Scheme 1

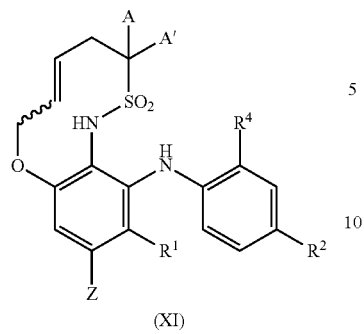

(XI)

$R^5 = C_1-C_6$ alkyl or alkenyl

In this scheme, a nitro phenol of formula (III), either commercially available or prepared by nitration of the appropriate phenol precursor, is O-alkylated using a suitable alkylating agent such as an alkyl or alkenyl halide or sulfate (e.g., $R^5$-halo), in the presence of base such as potassium carbonate, to produce a compound of Formula (IV). This compound is then allowed to undergo a nucleophilic aromatic substitution reaction with the aniline of Formula (VI) in the presence of a strong non-nucleophilic base such as LHDMS, to provide the compound of Formula (VII). Reduction of the nitro group in the Formula (VII) compound is then carried out using a reducing agent such as sodium hydrosulfide (dithionite) to provide the compound of Formula (VIII). Sulfonylation of the Formula (VIII) compound using the sulfonyl chloride of Formula (IX) in the presence of a base such as pyridine, provides an intermediate of Formula (X). The sulfonyl chloride of Formula (IX) can be prepared by reaction of a haloalkene with sedum sulphite to form an alkene sulfonic acid which can be converted to the sulfonyl chloride by treatment with a suitable reagent such as oxalyl chloride.

Reaction of the Formula (X) compound when $R^5$ is allyl under metathesis conditions, i.e., in the presence of Zhang or Hoveyda-Grubs second generation catalyst, provides the compound of Formula (XI).

Additional transformations of the intermediates of Formula (X) and Formula (XI) are shown in Reaction Schemes 2-4 below.

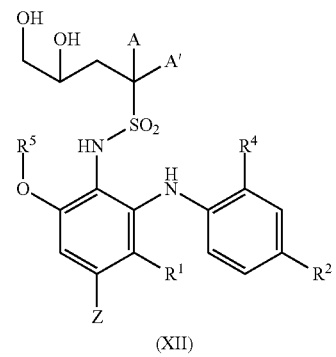

(XII)

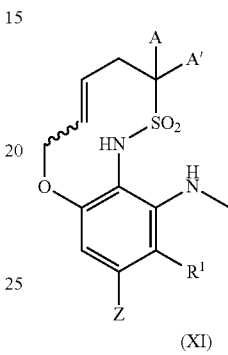

(XI)

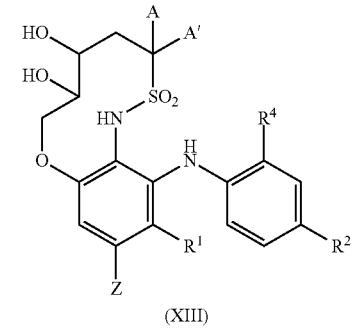

(XIII)
[(I), X, Y = OH, ----- = single bond]

Reaction Scheme 2 illustrates the subsequent oxidation of the Formula (X) compound with osmium tetroxide provides the compound of Formula (XII). Reaction of the Formula (XI) intermediate provides the compound of Formula (XIII) [Formula (I), where X, Y =OH and ==== represents a single bond].

Reaction Scheme 2

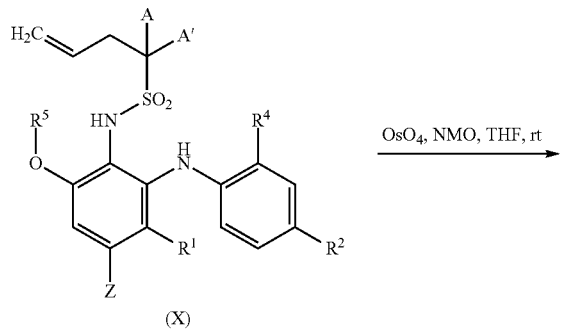

OsO4, NMO, THF, rt →

(X)

Reaction Scheme 3

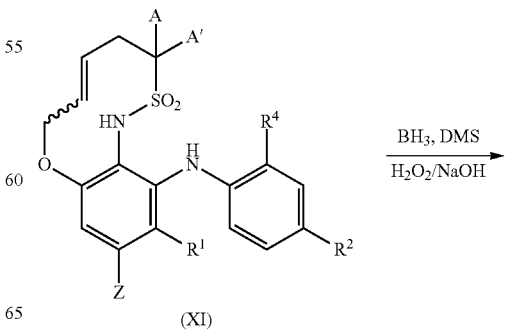

BH3, DMS
—————→
H2O2/NaOH (XI)

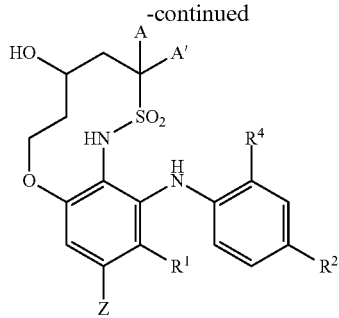

(XIVa)
[(I), X = OH, Y = H
----- represents a
single bond]

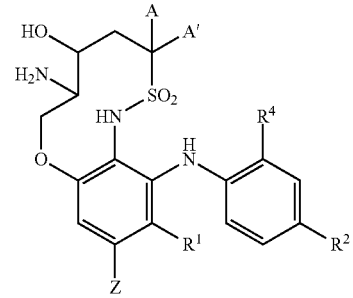

(XVb)
[(I), X = OH, Y = NH$_2$,
----- represents a
single bond]

Reaction Scheme 4 illustrates the preparation of Formula (I) compounds in which one of X and Y is OH, and the other of X and Y is NH$_2$. This is carried out by reaction of the compound of Formula (XI) with OsO$_4$ and silver nitrate in the presence of sodium t-butoxycarbonylchloramide. Both regioisomers, i.e., Formula (XVa) and Formula (XVb), are produced in this reaction.

The compounds of Formula (II) are prepared as shown by the method illustrated in Reaction Scheme 5:

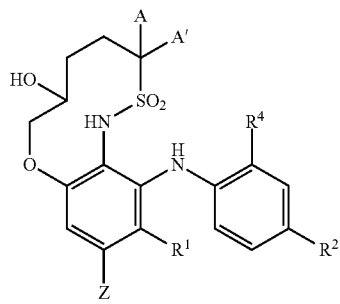

(XIVb)
[(I), X = OH, Y = H
----- represents a
single bond]

Reaction Scheme 3 illustrates the preparation of Formula (I) compounds in which one of X and Y is OH, and the other of X and Y is H. This is accomplished by reaction of the compound of Formula (XI) with BH$_3$-DMS complex and subsequent workup with H$_2$O$_2$/NaOH. Both regioisomers, i.e., Formula (XIVa) and Formula (XIVb), are produced in this reaction.

Reaction Scheme 4

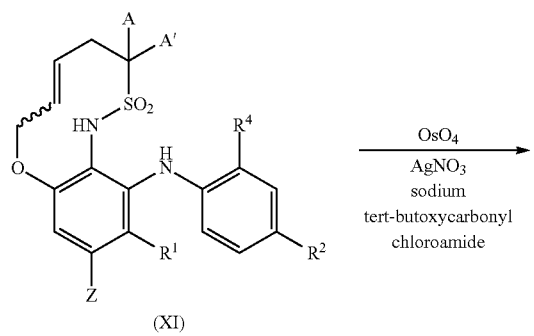

(XVa)
[(I), X = NH$_2$, Y = OH,
----- represents a
single bond]

Reaction Scheme 5

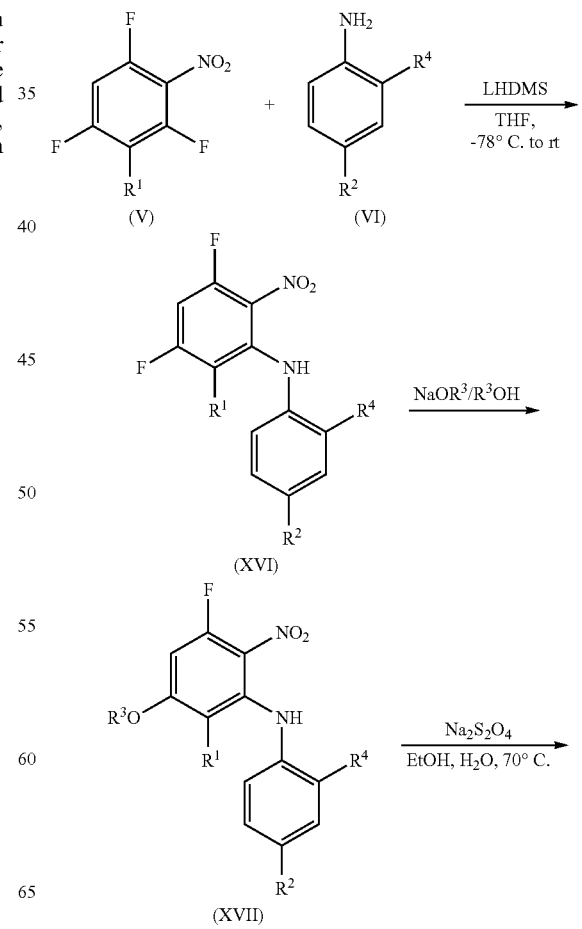

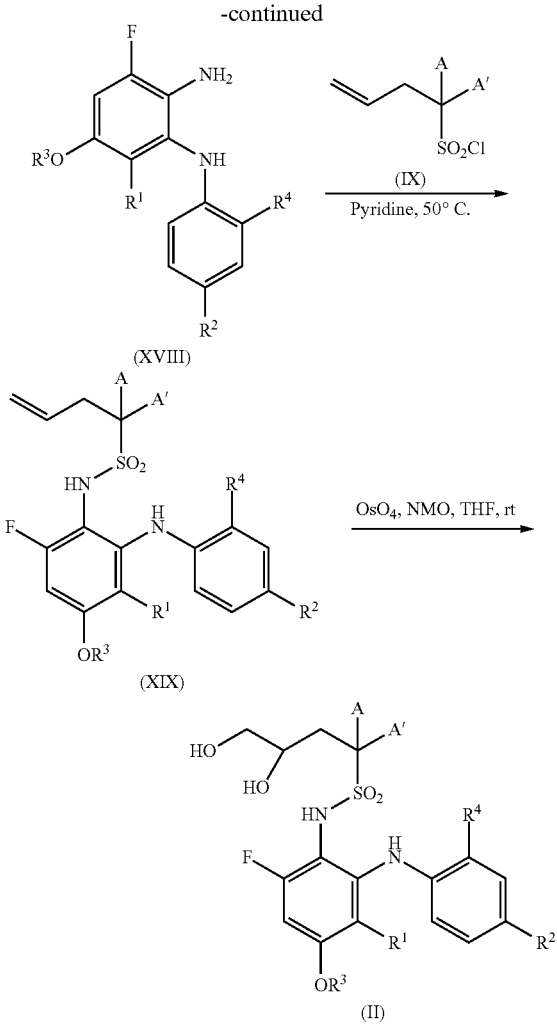

In this scheme, the tetrafluoronitrobenzene of Formula (V) is allowed to react with the aniline of Formula (VI) in a nucleophilic aromatic substitution reaction in the presence of a strong non-nucleophilic base such as LHDMS, to produce the biaryl aniline of Formula (XVI). A second nucleophilic substitution with an alkoxide ($R^3O^-$) is carried out to give the compound of Formula (XVII) with no other isomers formed. Reduction of the nitro group in compound of Formula (XVII) provides the compound of Formula (XVIII), and sulfonylation using the sulfonyl chloride of Formula (IX) provides the intermediate of Formula (XIX). Oxidation in a manner similar to that described in Reaction Scheme 2 gives the compound of Formula (II).

Thus, the isomeric compounds of Formula (II) [where $R^1$ is F, $R^2$ is F, $R^3$ is Me, and $R^4$ is F] and Formula (XII) [where $R^1$ is F, $R^2$ is I, Z is F, $R^4$ is F and $R^5$ is methyl] can be specifically and unambiguously prepared, depending on the reaction sequence employed.

Pharmaceutical Compositions

Describe herein are pharmaceutical compositions. In some embodiments, the pharmaceutical compositions comprise an effective amount of a compound of Formulae (I)-(II), or a pharmaceutically acceptable salt, solvate, hydrate or derivative thereof. In some embodiments, the pharmaceutical compositions comprise an effective amount of a compound of Formulae (I)-(II) and at least one pharmaceutically acceptable carrier. In some embodiments the pharmaceutical compositions are for the treatment of disorders. In some embodiments, the pharmaceutical compositions are for the treatment of disorders in a mammal.

MEK Modulation

Also described herein are methods of modulating MEK activity by contacting MEK with an amount of a compound of Formulae (I)-(II) sufficient to modulate the activity of MEK. Modulate can be inhibiting or activating MEK activity. In some embodiments, the invention provides methods of inhibiting MEK activity by contacting MEK with an amount of a compound of Formulae (I)-(II) sufficient to inhibit the activity of MEK. In some embodiments, the invention provides methods of inhibiting MEK activity in a solution by contacting said solution with an amount of a compound of Formulae (I)-(II) sufficient to inhibit the activity of MEK in said solution. In some embodiments, the invention provides methods of inhibiting MEK activity in a cell by contacting said cell with an amount of a compound described herein sufficient to inhibit the activity of MEK in said cell. In some embodiments, the invention provides methods of inhibiting MEK activity in a tissue by contacting said tissue with an amount of a compound described herein sufficient to inhibit the activity of MEK in said tissue. In some embodiments, the invention provides methods of inhibiting MEK activity in an organism by contacting said organism with an amount of a compound described herein sufficient to inhibit the activity of MEK in said organism. In some embodiments, the invention provides methods of inhibiting MEK activity in an animal by contacting said animal with an amount of a compound described herein sufficient to inhibit the activity of MEK in said animal. In some embodiments, the invention provides methods of inhibiting MEK activity in a mammal by contacting said mammal with an amount of a compound described herein sufficient to inhibit the activity of MEK in said mammal. In some embodiments, the invention provides methods of inhibiting MEK activity in a human by contacting said human with an amount of a compound described herein sufficient to inhibit the activity of MEK in said human.

Abnormal Cell Growth

Also described herein are compounds, pharmaceutical compositions and methods for inhibiting abnormal cell growth. In some embodiments, the abnormal cell growth occurs in a mammal. Methods for inhibiting abnormal cell growth comprise administering an effective amount of a compound of Formulae (I)-(II), or a pharmaceutically acceptable salt, solvate, hydrate or derivative thereof, wherein abnormal cell growth is inhibited. Methods for inhibiting abnormal cell growth in a mammal comprise administering to the mammal an amount of a compound of Formulae (I)-(II), or a pharmaceutically acceptable salt, solvate, hydrate or derivative thereof, wherein the amounts of the compound, salt, ester, prodrug, solvate, hydrate or derivative, is effective in inhibiting abnormal cell growth in the mammal.

In some embodiments, the methods comprise administering an effective amount of a compound of Formulae (I)-(II), or a pharmaceutically acceptable salt, ester, solvate, hydrate or derivative thereof, in combination with an amount of a chemotherapeutic, wherein the amounts of the compound, salt, solvate, hydrate or derivative, and of the chemotherapeutic are together effective in inhibiting abnormal cell growth. Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Also described are methods for inhibiting abnormal cell growth in a mammal comprising administering to the mammal an amount of a compound of Formulae (I)-(II), or a pharmaceutically acceptable salt, solvate, hydrate or derivative thereof, in combination with radiation therapy, wherein the amounts of the compound, salt, ester, prodrug, solvate, hydrate or derivative is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of Formulae (I)-(II) in this combination therapy can be determined as described herein.

The invention also relates to a method of and to a pharmaceutical composition of inhibiting abnormal cell growth in a mammal which comprises an amount of a compound of Formulae (I)-(II), or a pharmaceutically acceptable salt, ester, prodrug, solvate, hydrate or derivative thereof, or an isotopically-labeled derivative thereof, and an amount of one or more substances selected from antiangiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase. 9) inhibitors, and COX-2(cyclooxygenase 2) inhibitors, can be used in conjunction with a compound of the present invention and pharmaceutical compositions described herein. Examples of useful COX-2 inhibitors include CELEBREX™ (alecoxib), valdecoxib, and rofecoxib. Examples of useful matrix metalloproteinase inhibitors are described in WO 96133172 (published Oct. 24, 1996), WO 96127583 (published Mar. 7, 1996), European Patent Application No. 97304971.1 (filed Jul. 8, 1997), European Patent Application No. 99308617.2 (filed Oct. 29, 1999), WO 98107697 (published Feb. 26, 1998), WO 98103516 (published Jan. 29, 1998), WO 98134918 (published Aug. 13, 1998), WO 98134915 (published Aug. 13, 1998), WO 98133768 (published Aug. 6, 1998), WO 98130566 (published Jul. 16, 1998), European Patent Publication 606,046 (published Jul. 13, 1994), European Patent Publication 931,788 (published Jul. 28, 1999), WO 90105719 (published May 31, 1990), WO 99152910 (published Oct. 21, 1999), WO 99152889 (published Oct. 21, 1999), WO 99129667 (published Jun. 17, 1999), PCT International Application No. PCTIIB98I01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS13-0830.

Modes of Administration

Described herein are compounds of Formulae (I)-(II) or a pharmaceutically acceptable salt, or tautomer prodrug thereof. Also described, are pharmaceutical compositions comprising a compound of Formulae (I)-(II) or a pharmaceutically acceptable salt, solvate, or tautomer thereof. The compounds and compositions described herein may be administered either alone or in combination with pharmaceutically acceptable carriers, excipients or diluents, in a pharmaceutical composition, according to standard pharmaceutical practice.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, and rectal administration. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue. Those of ordinary skill in the art are familiar with formulation and administration techniques that can be employed with the compounds and methods of the invention. e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa.

The formulations include those suitable for oral, parenteral (including subcutaneous, intradermal, intramuscular, intravenous, intraarticular, and intramedullary), intra peritoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Pharmaceutical preparations for administration by inhalation are conveniently delivered from an insufflator, nebulizer pressurized packs or other convenient means of delivering & aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

The compounds or compositions described herein can be delivered in a vesicle, e.g., a liposome (see, for example, Langer, *Science* 1990, 249, 1527-1533; Treat et al., *Liposomes in the Therapy of Infectious Disease and Cancer*, Lopez-Bemstein and Fidler, Ed., Liss, N.Y., pp. 353-365, 1989). The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. *Surgery,* 1980 88, 507; Saudek et al. *N. Engl. J. Med.* 1989, 321, (574). Additionally, a controlled release system can be placed in proximity of the therapeutic target. (See, Goodson, *Medical Applications of Controlled Release,* 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and-a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention can be used. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regiment.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. The quantity of active compound in a unit dose of preparation may be varied or adjusted from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Combination Therapies

The compounds described herein or a pharmaceutically acceptable salt, solvate, or tautomer thereof may be administered as a sole therapy. The compounds described herein or a pharmaceutically acceptable salt, solvate, or tautomer thereof may also be administered in combination with another therapy or therapies.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds 1 compositions may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compound (and where appropriate, other therapeutic agent and/or radiation) will depend upon the diagnosis of the attending physicians and their judgment of the condition of the patient and the appropriate treatment protocol. Other therapeutic agents may include chemotherapeutic agents, such as anti-tumor substances, for example those selected from, mitotic inhibitors, for example vinblastine; alkylating agents, for example cisplatin, carboplatin and cyclophosphamide; anti-metabolites, for example 5-fluorouracil, cytosine arabinside and hydroxyurea, or, for example, one of the preferred anti-metabolites disclosed in European Patent Application No. 0239362 such as N-(p-[N-(3,4-dihydro-2-methyl-4-oxoquinazolin-6-ylmethyl)-N-methylamino-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

The compounds and compositions described herein (and where appropriate chemotherapeutic agent and/or radiation) may be administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete. Thus, in accordance with experience and knowledge, the practicing physician can modify each protocol for the administration of a compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Specific, non-limiting examples of possible combination therapies include use of the compounds of the invention with agents found in the following pharmacotherapeutic classifications as indicated below. These lists should not be construed to be closed, but should instead serve as illustrative examples common to the relevant therapeutic area at present. Moreover, combination regimens may include a variety of routes of administration and should include oral, intravenous, intraocular, subcutaneous, dermal, and inhaled topical.

For the treatment of oncologic diseases, proliferative disorders, and cancers, compounds according to the present invention may be administered with an agent selected from the group comprising: aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase inhibitors, IGF-I inhibitors, FGF3 modulators, mTOR inhibitors, Smac mimetics, HDAC inhibitors, agents that induce cell differentiation, bradykinin1 receptor antagonists, angiotensin-II antagonists, cyclooxygenase inhibitors, heparanase inhibitors, lymphokine inhibitors, cytokine inhibitors, IKK inhibitors, P38MAPK inhibitors, HSP90 inhibitors, multikinase inhibitors, bisphosphanates, rapamycin derivatives, ant-apoptotic pathway inhibitors, apoptotic pathway agonists, PPAR agonists, inhibitors of Ras isoforms, telomerase inhibitors, protease inhibitors, metalloproteinase inhibitors, and aminopeptidase inhibitors.

For the treatment of oncologic diseases, proliferative disorders, and cancers, compounds according to the present invention may be administered with an agent selected from the group comprising: dacarbazine (DTIc), actinomycins C, C, D, and F, cyclophosphamide, melphalan, estramustine, maytansinol, rifamycin, streptovaricin, doxorubicin, daunorubicin, epirubicin, idarubicin, detorubicin, caminomycin, idarubicin, epirubicin, esorubicin, mitoxantrone, bleomycins A, $A_2$, and B, camptothecin, Irinotecan®, Topotecan®, 9-aminocamptothecin, 10,II-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Herceptin®, Rituxan®, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

For the treatment of inflammatory diseases and pain, compounds according to the present invention may be administered with an agent selected from the group comprising: corticosteroids, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, and other agents, such as capsaicin.

For the treatment of inflammatory diseases and pain, compounds according to the present invention may be administered with an agent selected from the group comprising: betamethasone dipropionate (augmented and nonaugmented), betamethasone valerate, clobetasol propionate, prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocalne, EMLA Cream (Eutectic mixture of Local Anesthetics (lidocaine 2.5% and prilocalne 2.5%), guaifenesin, guaifenesin/ketoprofedcyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentidclonidine, gabapentin/carbamazepine, carbamazepinelcyclobenzaprine, antihypertensives including clonidine, codeine, loperamide, tramdol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab; nitric oxide synthase inhibitors, particularly inhibitors of inducible nitric oxide synthase; and other agents, such as capsaicin.

For the treatment of ophthalmologic disorders and diseases of the eye, compounds according to the present invention may be administered with an agent selected from the group comprising: beta-blockers, carbonic anhydrase inhibitors, alpha.- and .beta.-adrenergic antagonists including a1-adrenergic antagonists, alpha2 agonists, miotics, prostaglandin analogs, corticosteroids, and immunosuppressant agents.

For the treatment of ophthalmologic disorders and diseases of the eye, compounds according to the present invention may be administered with an agent selected from the group comprising: timolol, betaxolol, levobetaxolol, carteolol, levobunolol, propranolol, brinzolamide, dorzolamide, nipradilol, iopidine, brimonidine, pilocarpine, epinephrine, latanoprost, travoprost, bimatoprost, unoprostone, dexamethasone, prednisone, methylprednisolone, azathioprine, cyclosporine, and immunoglobulins.

For the treatment of autoimmune disorders, compounds according to the present invention may be administered with an agent selected from the group comprising: corticosteroids, immunosuppressants, prostaglandin analogs and antimetabolites.

For the treatment of autoimmune disorders, compounds according to the present invention may be administered with an agent selected from the group comprising: dexamethasome, prednisone, methylprednisolone, azathioprine, cyclosporine, immunoglobulins, latanoprost, travoprost, bimatoprost, unoprostone, infliximab, rutuximab and methotrexate.

For the treatment of metabolic disorders, compounds according to the present invention may be administered with an agent selected from the group comprising: insulin, insulin derivatives and mimetics, insulin secretagogues, insulin sensitizers, biguanide agents, alpha-glucosidase inhibitors, insulinotropic sulfonylurea receptor ligands, protein tyrosine phosphatase-1B (PTP-1B) inhibitors, GSK3 (glycogen synthase kinase-3) inhibitors, GLP-1 (glucagon like peptide-1), GLP-1 analogs, DPPIV (dipeptidyl peptidase IV) inhibitors, RXR ligands sodium-dependent glucose co-transporter inhibitors, glycogen phosphorylase A inhibitors, an AGE breaker, PPAR modulators, and non-glitazone type PPARS agonist.

For the treatment of metabolic disorders, compounds according to the present invention may be administered with an agent selected from the group comprising: insulin, metformin, Glipizide, glyburide, Amaryl, meglitinides, nateglinide, repaglinide, PT-112, SB-517955, SB4195052, SB-216763, NN-57-05441, NN-57-05445, GW-0791, AGN-.sup.194.sup.204, T-1095, BAY R3401, acarbose Exendin-4, DPP728, LAF237, vildagliptin, MK-043 1, saxagliptin, GSK23A, pioglitazone, rosiglitazone, (R)-1-{4-[5-methyl-2-(4-trifluoromethyl-phenyl)-oxazol-4-ylmethoxy]-benzenesulfonyl)2,3-dihydro-1H-indole-2-carboxylic acid described in the patent application WO 031043985, as compound 19 of Example 4, and GI-262570.

Diseases

Described herein are methods of treating a disease in an individual suffering from said disease comprising administering to said individual an effective amount of a composition comprising a compound of Formulae (I)-(II) or a pharmaceutically acceptable salt, solvate, or, tautomer, thereof.

The invention also extends to the prophylaxis or treatment of any disease or disorder in which MEK kinase plays a role including, without limitation: oncologic, hematologic, inflammatory, ophthalmologic, neurological, immunologic, cardiovascular, and dermatologic diseases as well as diseases caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a MEK inhibitor for treating any such disease or disorder.

Diseases or disorders in which MEK kinase plays a role, either directly or via pro-inflammatory cytokines including the cytokines TNF, IL-1, IL-6 and IL-8, include, without limitation: dry eye, glaucoma, autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation, and conditions associated with prostaglandin endoperoxidase synthetase-2 (COX-2).

In certain aspects of the invention, the disease is a hyperproliferative condition of the human or animal body, including, but not limited to cancer, hyperplasias, restenosis, inflammation, immune disorders, cardiac hypertrophy, atherosclerosis, pain, migraine, angiogenesis-related conditions or disorders, proliferation induced after medical conditions, including but not limited to surgery, angioplasty, or other conditions.

In further embodiments, said hyperproliferative condition is selected from the group consisting of hematologic and nonhematologic cancers. In yet further embodiments, said hematologic cancer is selected from the group consisting of multiple myeloma, leukemias, and lymphomas. In yet further embodiments, said leukemia is selected from the group consisting of acute and chronic leukemias. In yet further embodiments, said acute leukemia is selected from the group consisting of acute lymphocytic leukemia (ALL) and acute nonlymphocytic leukemia (ANLL). In yet further embodiments, said chronic leukemia is selected from the group consisting of chronic lymphocytic leukemia (CLL) and chronic myelogenous leukemia (CML). In further embodiments, said lymphoma is selected from the group consisting of Hodgkin's lymphoma and non-Hodgkin's lymphoma. In further embodiments, said hematologic cancer is multiple myeloma. In other embodiments, said hematologic cancer is of low, intermediate, or high grade. In other embodiments, said nonhematologic cancer is selected from the group consisting of brain cancer, cancers of the head and neck, lung cancer, breast cancer, cancers of the reproductive system, cancers of the digestive system, pancreatic cancer, and cancers of the urinary system. In further embodiments, said cancer of the digestive system is a cancer of the upper digestive tract or colorectal cancer. In further embodiments, said cancer of the urinary system is bladder cancer or renal cell carcinoma. In further embodiments, said cancer of the reproductive system is prostate cancer.

Additional types of cancers which may be treated using the compounds and methods described herein include: cancers of oral cavity and pharynx, cancers of the respiratory system, cancers of bones and joints, cancers of soft tissue, skin cancers, cancers of the genital system, cancers of the eye and orbit, cancers of the nervous system, cancers of the lymphatic system, and cancers of the endocrine system. In certain embodiments, these cancer s may be selected from the group consisting of cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, and other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and cutaneous T-cell lymphoma, both granulocytic and monocytic.

Yet other types of cancers which may be treated using the compounds and methods described herein include: adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

Also described are methods for the treatment of a hyperproliferative disorder in a mammal that comprise administering to said mammal a therapeutically effective amount of a compound of Formulae (I)-(II)), or a pharmaceutically acceptable salt, solvate, hydrate or derivative thereof, in combination with an antitumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The disease to be treated using the compounds, compositions and methods described herein may be a hematologic disorder. In certain embodiments, said hematologic disorder is selected from the group consisting of sickle cell anemia, myelodysplastic disorders (MDS), and myeloproliferative disorders. In further embodiments, said myeloproliferative disorder is selected from the group consisting of polycythemia Vera, myelofibrosis and essential thrombocythemia.

The compounds, compositions and methods described herein may be useful as anti-inflammatory agents with the additional benefit of having significantly less harmful side effects. The compounds, compositions and methods described herein are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds, compositions and methods described herein are also useful in treating osteoporosis and other related bone disorders. These compounds, compositions and methods described herein can also be used to treat gastrointestinal conditions such as reflux esophagitis, diarrhea, inflammatory bowel disease, Crohn's disease, gastritis, irritable bowel syndrome and ulcerative colitis. The compounds, compositions and methods described herein may also be used in the treatment of pulmonary inflammation, such as that associated with viral infections and cystic fibrosis. In addition, the compounds, compositions and methods described herein are also useful in organ transplant patients either alone or in combination with conventional immunomodulators. Yet further, the compounds, compositions and methods described herein are useful in the treatment of pruritis and vitaligo. In particular, compounds, compositions and methods described herein are useful in treating the particular inflammatory disease rheumatoid arthritis.

Further inflammatory diseases which may be prevented or treated include, without limitation: asthma, allergies, respiratory distress syndrome or acute or chronic pancreatitis. Furthermore, respiratory system diseases may be prevented or treated including but not limited to chronic obstructive pulmonary disease, and pulmonary fibrosis. In addition, MEK kinase inhibitors described herein are also associated with prostaglandin endoperoxidase synthetase-2 (COX-2) production. Pro-inflammatory mediators of the cyclooxygenase pathway derived from arachidonic acid, such as prostaglandins, are produced by inducible COX-2 enzyme. Regulation of COX-2 would regulate these proinflammatory mediators, which affect a wide variety of cells and are important and critical inflammatory mediators of a wide variety of disease states and conditions. In particular, these inflammatory mediators have been implicated in pain, such as in the sensitization of pain receptors, and edema. Accordingly, additional MEK kinase-mediated conditions which may be prevented or treated include edema, analgesia, fever and pain such as neuromuscular pain, headache, dental pain, arthritis pain and pain caused by cancer.

Further, the disease to be treated by the compounds, compositions and methods described herein may be an ophthalmologic disorder. Ophthalmologic diseases and other diseases in which angiogenesis plays a role in pathogenesis, may be treated or prevented and include, without limitation, dry eye (including Sjogren's syndrome), macular degeneration, closed and wide angle glaucoma, retinal ganglion degeneration, occular ischemia, retinitis, retinopathies, uveitis, ocular photophobia, and of inflammation and pain associated with acute injury to the eye tissue. The compounds, compositions and methods described herein can be used to treat glaucomatous retinopathy andor diabetic retinopathy. The compounds, compositions and methods described herein can also be used to treat post-operative inflammation or pain as from ophthalmic surgery such as cataract surgery and refractive surgery. In further embodiments, said ophthalmologic disorder is selected from the group consisting of dry eye, closed angle glaucoma and wide angle glaucoma.

Further, the disease to be treated by the compounds, compositions and methods described herein may be an autoimmune disease. Autoimmune diseases which may be prevented or treated include, but are not limited to: rheumatoid arthritis, inflammatory bowel disease, inflammatory pain, ulcerative colitis, Crohn's disease, periodontal disease, temporomandibular joint disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs. host disease, and psoriasis. Inflammatory diseases which may be prevented or treated include, but are not limited to: asthma, allergies, respiratory distress syndrome or acute or chronic pancreatitis. In particular, compounds, compositions and methods described herein are useful in treating the particular autoimmune diseases rheumatoid arthritis and multiple sclerosis.

Further, the disease to be treated by the compounds, compositions and methods described herein may be a dermatologic disorder. In certain embodiments, said dermatologic disorder is selected from the group including, without limitation, melanoma, base1 cell carcinoma, squamous cell carcinoma, and other non-epithelial skin cancer as well as psoriasis and persistent itch, and other diseases related to skin and skin structure, may be treated or prevented with MEK kinase inhibitors of this invention.

Metabolic diseases which may be treated or prevented include, without limitation, metabolic syndrome, insulin resistance, and Type 1 and Type 2 diabetes. In addition, the compositions described herein can be used to treat insulin resistance and other metabolic disorders such as atherosclerosis that are typically associated with an exaggerated inflammatory signaling.

The compounds, compositions and methods described herein are also useful in treating tissue damage in such diseases as vascular diseases, migraine headaches, periarteritisnodosa, thyroiditis, aplastic anemia, Hodgkin's disease, sclerodoma, rheumatic fever, type I diabetes, neuromuscular junction disease including myasthenia gravis_white matter disease including multiple sclerosis, sarcoidosis, nephritis, nephrotic syndrome, Behcet's syndrome, polymyositis, gingivitis, periodontis, hypersensitivity, swelling occurring after injury, ischemias including myocardial ischemia, cardiovascular ischemia, and ischemia secondary to cardiac arrest, and the like. The compounds, compositions and methods described herein can also be used to treat allergic rhinitis, respiratory distress syndrome, endotoxin shock syndrome, and atherosclerosis.

Further, the disease to be treated by the compounds, compositions and methods described herein may be a cardiovascular condition. In certain embodiments, said cardiovascular condition is selected from the group consisting of atherosclerosis, cardiac hypertrophy, idiopathic cardiomyopathies, heart failure, angiogenesis-related conditions or disorders, and proliferation induced after medical conditions, including, but not limited to restenosis resulting from surgery and angioplasty.

Further, the disease to be treated by the compounds, compositions and methods described herein may be a neurological disorder. In certain embodiments, said neurologic disorder is selected from the group consisting of Parkinson's disease, Alzheimer's disease, Alzheimer's dementia, and central nervous system damage resulting from stroke, ischemia and trauma. In other embodiments, said neurological disorder is selected from the group consisting of epilepsy, neuropathic pain, depression and bipolar disorders.

Further, the disease to be treated by the compounds, compositions and methods described herein may cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, the compounds and compositions are for the treatment of a non-cancerous hyperproliferative disorder such as benign hyperplasia of the skin (e.g., psoriasis), restenosis, or prostate (e.g., benign prostatic hypertrophy (BPH)).

Further, the disease to be treated by the compounds, compositions and methods described herein may pancreatitis, kidney disease (including proliferative glomerulonephritis and diabetes-induced renal disease), pain, a disease related to vasculogenesis or angiogenesis, tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidemoid cancer in a mammal.

Further, the disease to be treated by the compounds, compositions and methods described herein may the prevention of blastocyte implantation in a mammal.

Patients that can be treated with the compounds ester, prodrug, solvate, hydrate or derivative of said compounds, according to the methods of this invention include for example, patients that have been diagnosed as having described herein, or a pharmaceutically acceptable salt, psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, and myeloproliferative disorders; bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Miillerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed andor promoted to health providers, including physicians, nurses, pharmacists, formulary officials, and the like. Kits may also, in some embodiments, be marketed directly to the consumer.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals, exotic animals and farm animals, including mammals, rodents, and the like. More preferred animals include horses, dogs, and cats.

In general, the compounds used in this invention may be prepared by standard techniques known in the art, by known processes analogous thereto, and/or by the processes described herein, using starting materials which are either commercially available or producible according to routine, conventional chemical methods. The following preparative methods are presented to aid the reader in the synthesis of the compounds of the present invention.

EXPERIMENTAL EXAMPLES

General Experimental Methods

Air and moisture sensitive liquids and solutions were transferred via syringe or cannula, and introduced into reaction vessels through rubber septa. Commercial grade reagents and solvents were used without further purification. The term "concentration under reduced pressure" or "in vacuo" refers to use of a Buchi rotary evaporator at approximately 15 mm of Hg. All temperatures are reported uncorrected in degrees Celsius (° C.).

When degassing of a solution was performed, it was accomplished by bubbling nitrogen gas through the solution.

Thin layer chromatography (TLC) was performed on EM Science pre-coated glass-packed silica gel 60 A F-254 250 pm plates. Column chromatography (flash chromatography) was performed on a Combiflash system using 32-63 micron, 60 Å, silica gel pre-packed cartridges. Purification using preparative reversed-phase HPLC chromatography was accomplished using a Gilson 215 system, using a YMC Pro-C18 AS-342 (150×20 mm I.D.) column. Typically, the mobile phase used was a mixture of $H_2O$ (A) and MeCN (B). The water may be mixed with 0.1% TFA. A typical gradient is described below:

HPLC method (method H): Phenomenex C18 (150×30 mm) 5μ column, 5% acetonitrile to 90% acetonitrile over 20 min, flow 20 mL/min LC-MS/MS Method: Zorbax C18 (15 cm×2.1 mm) column, Solvent A: acetonitrile with 0.1% formic acid, Solvent B: water with 0.1% formic acid, gradient 5% A to 85% A over 15 min.

Routine one-dimensional NMR spectroscopy was performed on 400 or 500 MHz Varian Mercury-plus spectrometers. The samples were dissolved in deuterated solvents obtained from Cambridge Isotope Labs, and transferred to 5 mm ID Wilmad NMR tubes. The spectra were acquired at 293° K. The chemical shifts were recorded on the ppm scale and were referenced to the appropriate residual solvent signals, such as 2.49 ppm for DMSO-$d_6$, 1.9 3 ppm for $CD_3CN$, 3.30 ppm for $CD_3OD$, 5.32 ppm for $CD_2Cl_2$, and 7.26 ppm for $CDCl_3$ for 'H spectra, and 39.5 ppm for DMSO-$d_6$, 1.3 ppm for $CD_3CN$, 49.0 ppm for $CD_3OD$, 53.8 ppm for $CD_2Cl_2$, and 77.0 ppm for $CDCl_3$ for $^{13}C$ spectra.

General methods of preparation are illustrated in the reaction schemes, and by the specific preparative examples that follow.

ABBREVIATIONS AND ACRONYMS

When the following abbreviations are used herein, they have the following meaning:
AcOH acetic acid
anhy anhydrous
Bu butyl
n-BuOH n-butanol
t-BuOH tert-butanol
t-BuOK potassium-tert-butoxide
CBS Corey-Bakshi-Shibata catalyst
$CD_3OD$ methanol-$d_4$
CI-MS chemical ionization mass spectrometry
conc concentrated
DCC dicyclohexylcarbodiimide
DCM dichloromethane
DMAP 4-dimethylaminopyridine
DME 1,2-dimethoxyethane
DMF N,N-dimethylformamide
DMSO dimethyl sulfoxide
ee enantiomeric excess
EI-MS electron impact mass spectrometry
ES-MS electrospray mass spectrometry
$Et_3N$ triethylamine
EtOAc ethyl acetate
EtOH ethanol
$Et_2O$ ethyl ether
GC-MS gas chromatography-mass spectrometry
h hour(s)
HPLC high-pressure liquid chromatography
IL-1 (2,3,4,n) interleukin-1 (2,3,4,n) protein
LC-MS liquid chromatography-mass spectrometry
LG leaving group
LHMDS Lithium bis(trimethylsilyl)amide
Me methyl
MeOH methanol
mg milligram
min minute(s)
mL milliliter
mmol millimole
NMR nuclear magnetic resonance
NMO N-methyl morpholine-N-oxide
ppm part per million
$R_f$ retention factor
$t_R$ retention time
rt room temperature
THF tetrahydrofuran
TFA trifluoroacetic acid
TLC thin layer chromatography
UV ultraviolet The following specific examples are presented to illustrate the invention described herein, but they should not be construed as limiting the scope of the invention in any way.

EXPERIMENTAL EXAMPLES

Intermediate 1

Preparation of Sodium Salt of But-3-ene-1-sulfonic acid

A solution of 4-bromo-1-butene (1.0 g, 7.4 mmol) and sodium sulphite (1.12 g, 8.88 mmol) in water (7 mL) was refluxed for 16 h. The reaction mixture was extracted with diethyl ether and aqueous layer was concentrated to yield but-3-ene-1-sulfonic acid (2.13 g). $^1$H-NMR (400 MHz, D2O, SODIUM SALT): δ 2.30-2.36 (2H, m), 2.82-2.85 (2H, m), 4.91 (1H, dd, J=10, 1.2), 5.00 (1H, dd, J=17.2, 1.6), 5.72-5.79 (1H, m).

Intermediate 2

Preparation of Sulfonylchloride of But-3-ene-1-sulfonic acid Sodium salt

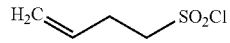

Sodium but-3-ene-1-sulfonate (Intermediate 1, 7.0 g) was added to cold oxalyl chloride (70 mL) at 0° C. The reaction mixture was warmed to rt and DMF (1 mL) was added dropwise over a period of 10 min into the reaction mixture, which was stirred at rt for 3 h. Excess of oxalyl chloride was removed under reduced pressure and residue dissolved in diethyl ether. The ether layer was separated and concentrated to yield but-3-ene-1-sulfonyl chloride (4.5 g). $^1$H-NMR (400

MHz, CDCl$_3$): δ 2.76-2.82 (2H, m), 3.71-3.75 (2H, m), 5.19-5.24 (2H, m), 5.78-5.83 (1H, m).

Intermediate 3

Preparation of 3,5-Difluoro-2-nitrophenol

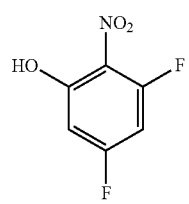 [SMILES: O=[N+]([O-])c1c(O)cc(F)cc1F]

To an ice-cooled stirred solution of 3,5-difluorophenol (2.0 g, 13.5 mmol) in glacial acetic acid (12 mL) was dropwise added concentrated nitric acid (2.0 mL, 70%). Upon complete addition, the reaction mixture was warmed to room temperature and stirred for 1 h. The progress of reaction was monitored by TLC. After completion, the reaction mixture was poured into ice-water and aqueous layer extracted with ethyl acetate. The organic layer was washed with water a couple of times, dried over anhydrous Na$_2$SO$_4$ and concentrated to yield a mixture of 3,5-difluoro-2-nitrophenol and 3,5-difluoro-4-nitrophenol (3.5 g), which was used further without purification.

Intermediate 4

Preparation of 3,4,5-Trifluoro-1-nitrophenol

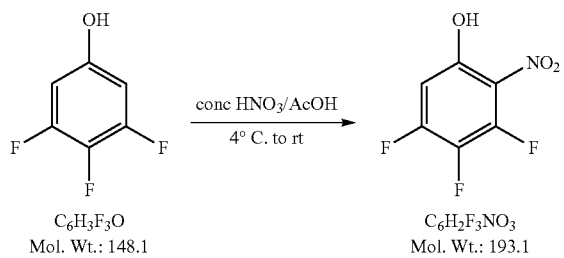 [SMILES: Oc1cc(F)c(F)c(F)c1 ; O=[N+]([O-])c1c(O)cc(F)c(F)c1F]

3,4,5-Trifluorophenol (14.81 g, 0.1 mol) was dissolved in glacial acetic acid (50 mL) and cooled to 4° C. while concentrated nitric acid (5 mL, 70%) was added dropwise over 15 min, during which time the color of the mixture becomes yellow. Upon complete addition of HNO$_3$, the reaction mixture was allowed to warm to room temperature and stirred for an additional 30 min. TLC analysis of an aliquot extracted into ethyl acetate indicates that a new non-polar spot was formed and the complete consumption of starting material. The mixture was then diluted with ethyl acetate (200 mL), transferred to separatory funnel, and washed copiously with water (3×100 mL). The organic layer was finally washed with brine, dried over anhyd MgSO$_4$, and evaporated under reduced pressure to afford crude product as a yellowish oil. (17.3 g, 90%). This crude material was used directly in the subsequent reaction described in Intermediate 6. $^1$H NMR (400 MHz, CDCl$_3$): 6.84 (m, 1H, ArH), 10.28 (brs, 1H, OH).

Intermediate 5

Synthesis of Allylether of 3,5-Difluoro-2-nitrophenol

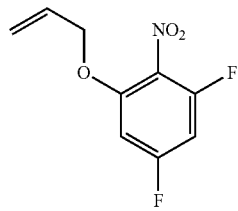

A solution of 3,5-difluoro-2-nitrophenol and 3,5-difluoro-4-nitrophenol (3.54 g, 20 mmol), allyl bromide (2.9 g, 24 mmol) and potassium carbonate (8.3 g, 60 mmol) in acetone (50 mL) was refluxed for 2 h. The progress of reaction was monitored by TLC. After completion, the reaction mixture was concentrated under reduced pressure at 25° C. The residue was diluted with water extracted with ether. The organic layer was washed with water, dried over anhydrous Na$_2$SO$_4$ and concentrated under reduced pressure at 25° C. The residue obtained was purified by silica gel column chromatography (0-1% ethyl acetate-hexane) to yield 1-(allyloxy)-3,5-difluoro-2-nitrobenzene (934 mg). $^1$H-NMR (400 MHz, CD$_3$OD): δ 4.72 (2H, d), 5.32 (1H, d J=10.8), 5.42 (1H, d, J=17.2), 5.98-6.02 (1H, m), 6.85 (1H, dt), 6.96 (1H, d).

Intermediate 6

Preparation of 3,4,5-Trifluoro-2-nitro-phenyl Allyl Ether

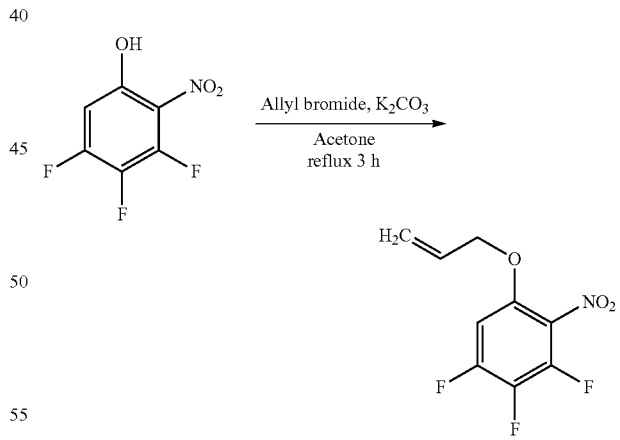

To a solution of crude 3,4,5-trifluoro-2-nitrophenol (Intermediate 4, 4.8 g, 25 mmol) in acetone (25 mL) was added K$_2$CO$_3$ (50 mmol) and allyl bromide (3.6 g, 30 mmol), and the mixture was heated to reflux for 2 h. TLC analysis of the reaction mixture (25 EtOAc:Hexanes) at this time reveals all starting material was consumed and the presence of a non-polar spot. The heating was discontinued and the reaction mixture was allowed to cool. Most of the acetone was evaporated under vacuo, and the remaining residue was diluted with ether (50 mL) and washed successively with water. The organic ether layer was dried over MgSO₄ and concentrated in vacuo by rotary evaporation. The crude yellow-orange oil was further purified by flash column chromatography over silica gel using hexanes to 15% hexanes:ethyl acetate gradient. The homogenous fractions from TLC were collected, combined and evaporated under reduced pressure to yield the allyl ether product (5.5 g, 95%) $^1$H NMR (400 MHz, CDCl₃): 4.65 (dt, J=1.6, 5.2 Hz, 2H, OCH₂), 5.39 (d, J=12.0 Hz, 1H, =CH₂), 5.45 (d, J=18.0 Hz, 1H, =CH₂), 5.98 (m, 1H, =CH), 6.72 (m, 1H, ArH).

Intermediate 7

Synthesis of (3-Allyloxy-5,6-difluoro-2-nitro-phenyl)-(2-fluoro-4-iodo-phenyl)-amine

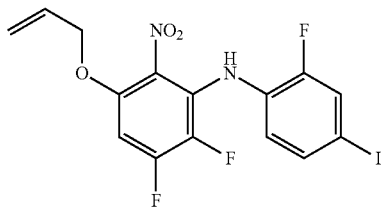 [SMILES: C=CCOc1cc(F)c(F)c(Nc2ccc(I)cc2F)c1[N+](=O)[O-]]

To a solution of 2-fluoro-4-iodo-phenylamine (1.1 g, 4.6 mmol) in THF (50 mL) was dropwise added LHMDS solution (6.0 mL, 6.0 mmol, 1 M in THF) at −78° C. After stirring for 1 h at −78° C., a solution of 1-allyloxy-3,4,5-trifluoro-2-nitrobenzene (1.2 g, 5.1 mmol) in THF (10 mL) was dropwise added into the reaction mixture. The reaction mixture was stirred at −78° C. for additional 1 h and brought to room temperature and stirred for 16 h. The progress of reaction was monitored by $^1$H NMR. After completion, the solvent was removed under reduced pressure. The residue obtained was dissolved in ethyl acetate, washed with water, dried over anhydrous Na₂SO₄ and concentrated. The residue was triturated with hexane to yield (3-allyloxy-5,6-difluoro-2-nitro-phenyl)-(2-fluoro-4-iodo-phenyl)-amine as a yellow solid (900 mg). $^1$H-NMR (400 MHz, CDCl₃): δ 4.62 (2H, d, J=4.8), 5.33-5.36 (1H, d, J=10), 5.48 (1H, d, J=17.2), 5.98-6.02 (1H, m), 6.22 (1H, dd, J=2.4, 9.6), 6.36 (1H, dd, J=2, 10.4), 7.04-7.08 (1H, m), 7.45-7.52 (2H, m), 7.79 (1H, s).

Intermediate 8

Synthesis of (3-allyloxy-5,6-difluoro-2-nitro-phenyl)-(4-bromo-2-fluoro-phenyl)-amine

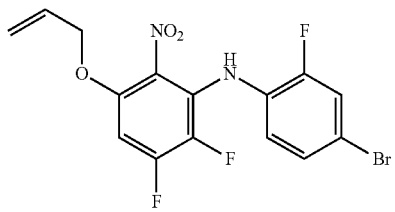

To a solution of 4-bromo-2-fluoro-phenylamine (0.815 g, 4.3 mmol) in THF (50 mL) was dropwise added LHMDS solution (5.6 mL, 5.6 mmol, 1 M in THF) at −78° C. After stirring for 1 h at −78° C., a solution of 1-allyloxy-3,4,5-trifluoro-2-nitro-benzene (1.1 g, 4.7 mmol) in THF (10 mL) was dropwise added into the reaction mixture, which was stirred at −78° C. for 1 h and at room temperature for 16 h. The progress of reaction was monitored by $^1$H NMR. After completion, the solvent was removed under reduced pressure. The residue was dissolved in ethyl acetate, washed with water, dried over anhydrous Na₂SO₄ and concentrated. The residue obtained was triturated with hexane to yield (3-allyloxy-5,6-difluoro-2-nitro-phenyl)-(4-bromo-2-fluoro-phenyl)-amine as a yellow solid (724 mg). $^1$H-NMR (400 MHz, CDCl₃): δ 4.55 (2H, d, J=5.6), 5.32-5.36 (2H, m), 5.42 (1H, d), 6.02-6.08 (1H, m), 6.35 (1H, t, J=8.8), 6.60-6.65 (1H, m), 7.06 (1H, d, J=8.4), 7.23 (1H, dd, J=2.0, 10.4).

Intermediate 9

Synthesis of (3-Allyloxy-5,6-difluoro-2-nitro-phenyl)-(4-iodo-phenyl)-amine

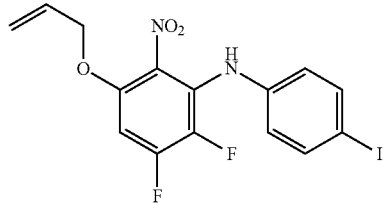 [SMILES: C=CCOc1cc(F)c(F)c(Nc2ccc(I)cc2)c1[N+](=O)[O-]]

To a solution of 4-iodophenylamine (0.940 g, 4.3 mmol) in THF (50 mL) was dropwise added LHMDS solution (5.6 mL, 5.6 mmol, 1 M in THF) at −78° C. After stirring for 1 h at −78° C., a solution of 1-allyloxy-3,4,5-trifluoro-2-nitro-benzene (1.1 g, 4.7 mmol) in THF (10 mL) was added dropwise into the reaction mixture, which was stirred at −78° C. for 1 h and at room temperature for 16 h. The progress of reaction was monitored by $^1$H NMR. After completion, the reaction mixture was concentrated under reduced pressure. The residue was dissolved in ethyl acetate, washed with water, dried over anhydrous Na₂SO₄ and concentrated. The residue obtained was triturated with hexane to yield (3-allyloxy-5,6-difluoro-2-nitro-phenyl)-(4-iodo-phenyl)-amine as an orange solid (1.1 g). $^1$H-NMR (400 MHz, CDCl₃): δ 4.54 (2H, d, J=4.8), 5.24 (1H, s), 5.32 (1H, d, J=10.8), 5.42 (1H, d, J=17.2), 6.06-6.02 (1H, m), 6.45 (2H, d, J=8.4), 6.57-6.62 (1H, m), 7.47 (2H, d, J=8.4).

Intermediate 10

Synthesis of (3-Allyloxy-5,6-difluoro-2-nitro-phenyl)-(2-chloro-4-iodo-phenyl)-amine

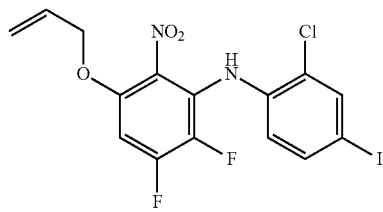 [SMILES: C=CCOc1cc(F)c(F)c(Nc2ccc(I)cc2Cl)c1[N+](=O)[O-]]

To solution of 2-chloro-4-iodo-phenylamine (1.09 g, 4.3 mmol) in THF (50 mL) was dropwise added LHMDS solution (5.6 mL, 5.6 mmol, 1 M in THF) at −78° C. After stirring for 1 h at −78° C., a solution of 1-allyloxy-3,4,5-trifluoro-2-nitro-benzene (1.1 g, 4.7 mmol) in THF (10 mL) was added dropwise into the reaction mixture, which was stirred at −78° C. for 1 h and at room temperature for 16 h. The progress of reaction was monitored by $^1$H NMR. After completion, the solvent was removed under reduced pressure. The residue was dissolved in ethyl acetate, washed with water, dried over anhydrous $Na_2SO_4$ and concentrated. The residue obtained was re-crystallized in hexane to yield (3-allyloxy-5,6-difluoro-2-nitro-phenyl)-(2-chloro-4-iodo-phenyl)-amine as an orange solid (843 mg). $^1$H-NMR (400 MHz, CDCl$_3$): δ 4.63 (2H, d, J=5.2), 5.37 (1H, d, J=10.4), 5.46 (1H, d, J=17.2) 5.96-6.00 (1H, m), 6.50-6.54 (1H, m), 6.60-6.65 (1H, m), 7.04 (1H, s), 7.43 (1H, d, J=8), 7.68 (1H, d, J=2).

Intermediate 11

Synthesis of N-(3-(Allyloxy)-5-fluoro-2-nitrophenyl)-2-fluoro-4-iodobenzenamine

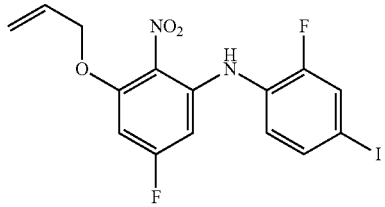 [SMILES: C=CCOc1cc(F)cc(Nc2ccc(I)cc2F)c1[N+](=O)[O-]]

To a solution of 2-fluoro-4-iodoaniline (933 mg, 3.94 mmol) in THF (10 mL) was drop wise added LHMDS solution (5.1 mL, 5.1 mmol, 1 M in THF) at −78° C. After stirring at −78° C. for 30 min, a solution of 2-nitro-3,5-difluorphenylallyl ether (934 mg, 4.3 mmol) in THF (5 mL) was added drop wise to into the reaction mixture, which was slowly warmed to room temperature and stirred for 16 h. After completion (as indicated by TLC), the reaction mixture was quenched with water and extracted with ether. The organic layer was dried over anhydrous $Na_2SO_4$ and concentrated. The residue obtained was re-crystallized in hexane to yield N-(3-(allyloxy)-5-fluoro-2-nitrophenyl)-2-fluoro-4-iodobenzenamine (1.56 g). $^1$H-NMR (400 MHz, CDCl$_3$): δ 4.62 (2H, d, J=4.8), 5.33-5.36 (1H, d, J=10), 5.48 (1H, d, J=17.2), 5.98-6.02 (1H, m), 6.22 (1H, dd, J=2.4, 9.6), 6.36 (1H, dd, J=2, 10.4), 7.04-7.08 (1H, m), 7.45-7.52 (2H, m).

Intermediate 12

Synthesis of 2,3,5-Trifluoro-N-(2-fluoro-4-iodophenyl)-6-nitrobenzenamine

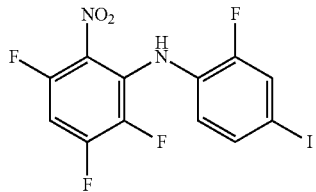 [SMILES: O=[N+]([O-])c1c(F)cc(F)c(F)c1Nc1ccc(I)cc1F]

To a solution of 2-fluoro-4-iodoaniline (1.0 g, 4.21 mmol) in THF (20 mL) was dropwise added LHMDS solution (5.1 mL, 5.1 mmol, 1 M in THF) at −78° C. After stirring at −78° C. for 30 min, a solution of 2,3,4,6-tetrafluoronitrobenzene (0.823 g, 4.21 mmol) in THF (5 mL) was added drop wise into the reaction mixture, which was slowly warmed to room temperature and stirred for 16 h. After completion (as indicated by TLC), the reaction mixture was quenched with water and extracted with ether. The organic layer was dried over anhydrous $Na_2SO_4$ and concentrated. The crude residue was triturated with hexane to yield 2,3,5-trifluoro-N-(2-fluoro-4-iodophenyl)-6-nitrobenzenamine (0.748 g). $^1$H-NMR (400 MHz, CDCl$_3$): δ 6.71-6.76 (2H, m), 7.40 (1H, d, J=8.8), 7.46 (1H, d, J=10), 7.69 (1H, s).

Intermediate 13

Synthesis of (4-Bromo-2-fluoro-phenyl)-(2,3,5-trifluoro-6-nitro-phenyl)-amine

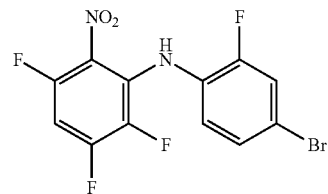 [SMILES: O=[N+]([O-])c1c(F)cc(F)c(F)c1Nc1ccc(Br)cc1F]

To a solution of 4-bromo-2-fluoro-phenylamine (2.0 g, 10.5 mmol) in THF (80 mL) was dropwise added LHMDS solution (12.6 mL, 12.6 mmol, 1 M in THF) at −78° C. After stirring at −78° C. for 1 h, a solution of 1,2,3,5-tetrafluoro-4-nitro-benzene (2.05 g, 10.5 mmol) in THF (20 mL) was added dropwise into the reaction mixture, which was stirred at −78° C. for 1 h, and at room temperature for 16 h. The progress of reaction was monitored by $^1$H NMR. After completion, the reaction mixture was concentrated under reduced pressure. The residue was dissolved in ethyl acetate, washed with water, dried over anhydrous $Na_2SO_4$ and concentrated. The residue obtained was re-crystallized in hexane to yield (4-bromo-2-fluoro-phenyl)-(2,3,5-trifluoro-6-nitro-phenyl)-amine as a yellow solid (1.6 g). $^1$H-NMR (400 MHz, CDCl$_3$): δ 6.73-6.75 (1H, m), 6.86-6.87 (1H, m), 7.22 (1H, d, J=8.4), 7.30 (1H, dd, J=2.0 Hz, 10.8), 7.71 (1H, s).

Intermediate 14

Synthesis of 2-Fluoro-N-(3,5-difluoro-2-nitrophenyl)-4-iodobenzenamine

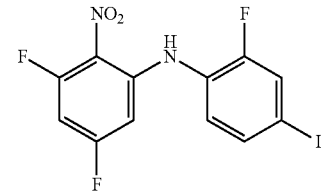 [SMILES: O=[N+]([O-])c1c(F)cc(F)cc1Nc1ccc(I)cc1F]

To a solution of 2-fluoro-4-iodoaniline (1.0 g, 4.21 mmol) in THF (20 mL) was dropwise added LHMDS solution (5.1 mL, 5.1 mmol, in 1 M THF) at −78° C. After stirring at −78° C. for 30 min, a solution of 2,4,6-trifluoronitrobenzene (0.747 g, 4.21 mmol) in THF (5 mL) was added dropwise into the reaction mixture, which was slowly warmed to room temperature and stirred for 16 h. After completion (as indicated by TLC), the reaction mixture was quenched with water and extracted with ether. The organic layer was dried over anhydrous Na₂SO₄ and concentrated. The residue was triturated with hexane to yield 2-fluoro-N-(3,5-difluoro-2-nitrophenyl)-4-iodobenzenamine (1.1 g). ¹H-NMR (400 MHz, CDCl₃): δ 6.42-6.47 (2H, m), 7.08 (1H, t, J=8.0 Hz), 7.52-7.58 (2H, m), 8.60 (1H, s).

Intermediate 15

2,5-Difluoro-N-(2-fluoro-4-iodophenyl)-3-methoxy-6-nitrobenzenamine

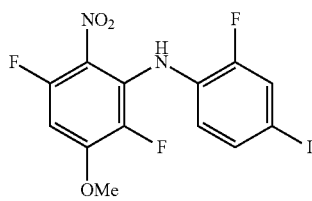 [SMILES: COc1cc(F)c([N+](=O)[O-])c(Nc2ccc(I)cc2F)c1F]

To a solution of 2,3,5-trifluoro-N-(2-fluoro-4-iodophenyl)-6-nitrobenzenamine (Intermediate 12. 700 mg, 1.7 mmol) in THF (20 mL) was added NaOMe solution at −78° C. (which was prepared by dissolving Na metal (39 mg, 1.7 mmol) in 4 mL of methanol). The reaction mixture was brought to rt and stirred for 1 h at same temperature. The progress of reaction was monitored by TLC. After completion, the reaction mixture was quenched with water and extracted with ether. The organic layer was dried over Na₂SO₄ and concentrated under reduced pressure. The residue was purified by flash column chromatography to yield 2,5-difluoro-N-(2-fluoro-4-iodophenyl)-3-methoxy-6-nitrobenzenamine as yellow solid (597 mg). ¹H-NMR (400 MHz, CDCl₃): δ 3.95 (3H, s), 6.51-6.56 (1H, m), 6.57-6.65 (1H, m), 7.34 (1H, d, J=8.8), 7.42 (1H, dd, J=1.6, 10), 7.7 (1H, s).

Intermediate 16

(4-Bromo-2-fluoro-phenyl)-(2,5-difluoro-3-methoxy-6-nitro-phenyl)-amine

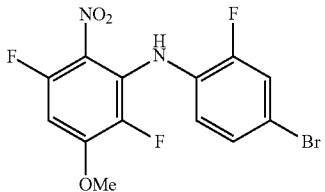 [SMILES: COc1cc(F)c([N+](=O)[O-])c(Nc2ccc(Br)cc2F)c1F]

To a solution of (4-bromo-2-fluoro-phenyl)-(2,3,5-trifluoro-6-nitro-phenyl)-amine (Intermediate 13, 1.5 g, 4.1 mmol) in THF (10 mL) was dropwise added NaOMe solution [prepared by dissolving Na metal (100 mg, 4.1 mmol) in methanol (10 mL)] at −78° C. After complete addition, the reaction mixture was warmed to room temperature and stirred for 1 h. The progress of reaction was monitored by TLC. After completion, the reaction mixture was concentrated under reduced pressure and residue obtained was purified by flash column chromatography to yield (4-bromo-2-fluoro-phenyl)-(2,5-difluoro-3-methoxy-6-nitro-phenyl)-amine as a yellow solid (912 mg).
¹H-NMR (400 MHz, CDCl₃): δ 3.95 (3H, s), 6.50-6.55 (1H, m), 6.77 (1H, m), 7.17 (1H, d, J=8.8), 7.25-7.28 (1H, m), 7.71 (1H, s).

Intermediate 17

2-Fluoro-N-(3-fluoro-5-methoxy-2-nitrophenyl)-4-iodobenzenamine

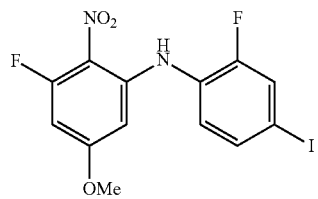 [SMILES: COc1cc(F)c([N+](=O)[O-])c(Nc2ccc(I)cc2F)c1]

To a solution of 2-fluoro-N-(3,5-difluoro-2-nitrophenyl)-4-iodobenzenamine (Intermediate 14, 1.05 g, 2.7 mmol) in THF (25 mL) was added NaOMe solution (prepared by dissolving Na metal (61 mg, 2.7 mmol) in 6 mL of methanol)-78° C. The reaction mixture was brought to rt and stirred for 1 h at same temperature. The progress of reaction was monitored by TLC. After completion, the reaction mixture was quenched with water and extracted with ether. The organic layer was dried over Na₂SO₄ and concentrated. The residue was purified by flash column chromatography to yield 2-fluoro-N-(3-fluoro-5-methoxy-2-nitrophenyl)-4-iodobenzenamine as yellow solid (584 mg). ¹H-NMR (400 MHz, CDCl₃): δ 3.91 (3H, s), 6.23 (1H, d, J=10.4), 6.35 (1H, d, J=10.8), 7.04-7.08 (1H, m), 7.45-7.52 (2H, m), 7.83 (1H, s).

Intermediate 18

6-Alllyloxy-3,4-difluoro-N2-(2-fluoro-4-iodo-phenyl)-benzene-1,2-diamine

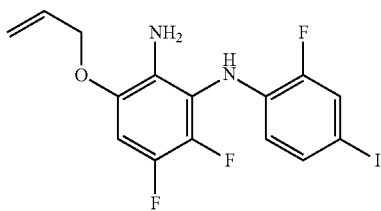

A suspension of (3-allyloxy-5,6-difluoro-2-nitro-phenyl)-(2-fluoro-4-iodo-phenyl)-amine (Intermediate 7, 0.9 g, 2 mmol) in ethanol (12 mL) was stirred at 70° C. to obtain a clear solution. To this hot solution, was added a freshly prepared solution of Na₂S₂O₄ (1.04 g, 6 mmol) in water (2.5 mL). The reaction mixture was stirred at 90° C. for 1 h. The progress of reaction was monitored by TLC. After completion, the solvent was removed under reduced pressure. The residue was diluted with ethyl acetate, washed with water, and the organic phase was dried over anhydrous Na₂SO₄ and concentrated to yield 6-allyloxy-3,4-difluoro-N2-(2-fluoro-4-iodo-phenyl)-benzene-1,2-diamine as a brown solid (730 mg). ¹H-NMR (400 MHz, CDCl₃): δ 3.86 (2H, bs), 4.54 (2H, d, J=5.2), 5.34 (1H, d, J=10.8), 5.42 (1H, d, J=17.2), 5.66 (1H, bs), 6.02-6.09 (1H, m), 6.20 (1H, d, J=8.4), 6.62-6.66 (1H, m), 7.33 (1H, dd, J=2, 8.4), 7.63 (1H, d, J=2).

Intermediate 19

6-Allyloxy-N2-(4-bromo-2-fluoro-phenyl)-3,4-difluoro-benzene-1,2-diamine

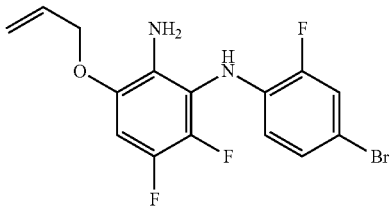 [SMILES: C=CCOc1cc(F)c(F)c(Nc2ccc(Br)cc2F)c1N]

A suspension of (3-allyloxy-5,6-difluoro-2-nitro-phenyl)-(4-bromo-2-fluoro-phenyl)-amine (Intermediate 8, 0.7 g, 1.7 mmol) in ethanol (12 mL) was stirred at 70° C. to obtain a clear solution. To this hot solution, was added a freshly prepared solution of $Na_2S_2O_4$ (0.9 g, 5.2 mmol) in water (1.9 mL) and stirred the reaction mixture at 90° C. for 1 h. The progress of reaction was monitored by TLC. After completion, the solvent was removed under reduced pressure. The residue was dissolved in ethyl acetate, washed with water, dried over anhydrous $Na_2SO_4$ and concentrated to yield 6-allyloxy-N2-(4-bromo-2-fluoro-phenyl)-3,4-difluoro-benzene-1,2-diamine as a yellow solid (630 mg). $^1$H-NMR (400 MHz, $CDCl_3$): δ 4.55 (2H, d, J=5.6), 5.32-5.36 (2H, m), 5.42 (1H, d), 6.02-6.08 (1H, m), 6.35 (1H, t, J=8.8), 6.60-6.65 (1H, m), 7.06 (1H, d, J=8.4), 7.23 (1H, dd, J=2.0, 10.4).

Intermediate 20

6-Allyloxy-3,4-difluoro-N2-(4-iodo-phenyl)-benzene-1,2-diamine

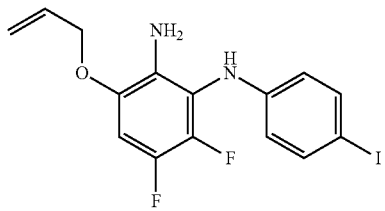

A suspension of (3-allyloxy-5,6-difluoro-2-nitro-phenyl)-(4-iodo-phenyl)-amine (Intermediate 9, 1.1 g, 2.5 mmol) in ethanol (15 mL) was stirred at 70° C. to obtain a clear solution. To this hot solution, was added a freshly prepared solution of $Na_2S_2O_4$ (1.3 g, 7.6 mmol) in water (3.1 mL) and stirred the reaction mixture at 90° C. for 1 h. The progress of reaction was monitored by TLC. After completion, the solvent was removed under reduced pressure. The residue was dissolved in ethyl acetate, washed with water, and the organic phase was dried over anhydrous $Na_2SO_4$ and concentrated to yield 6-allyloxy-3,4-difluoro-N2-(4-iodo-phenyl)-benzene-1,2-diamine as a brown solid (620 mg). $^1$H-NMR (400 MHz, $CDCl_3$): δ 4.54 (2H, d, J=4.8), 5.24 (1H, s), 5.32 (1H, d, J=10.8), 5.42 (1H, d, J=17.2), 6.06-6.02 (1H, m), 6.45 (2H, d, J=8.4), 6.57-6.62 (1H, m), 7.47 (2H, d, J=8.4).

Intermediate 21

6-Allyloxy-N2-(2-chloro-4-iodo-phenyl)-3,4-difluoro-benzene-1,2-diamine

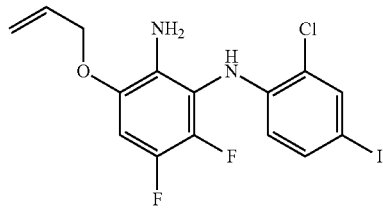

A suspension of (3-allyloxy-5,6-difluoro-2-nitro-phenyl)-(2-chloro-4-iodo-phenyl)-amine (Intermediate 10, 0.823 g, 1.8 mmol) in ethanol (12 mL) was stirred at 70° C. to obtain a clear solution. To this hot solution, was added a freshly prepared solution of $Na_2S_2O_4$ (0.920 g, 5.3 mmol) in water (2.4 mL) and stirred the reaction mixture at 90° C. for 1 h. The progress of reaction was monitored by TLC. After completion, the solvent was removed under reduced pressure. The residue was dissolved in ethyl acetate, washed with water, and the organic phase was dried over anhydrous $Na_2SO_4$ and concentrated to yield 6-allyloxy-N2-(2-chloro-4-iodo-phenyl)-3,4-difluoro-benzene-1,2-diamine as an off-white solid (570 mg). $^1$H-NMR (400 MHz, $CDCl_3$): δ 3.86 (2H, bs), 4.54 (2H, d, J=5.2), 5.34 (1H, d, J=10.8), 5.42 (1H, d, J=17.2), 5.66 (1H, bs), 6.02-6.09 (1H, m), 6.20 (1H, d, J=8.4), 6.62-6.66 (1H, m), 7.33 (1H, dd, J=2, 8.4), 7.63 (1H, d, J=2).

Intermediate 22

6-Allyloxy-3-fluoro-N2-(2-fluoro-4-iodo-phenyl)-4-methoxy-benzene-1,2-diamine

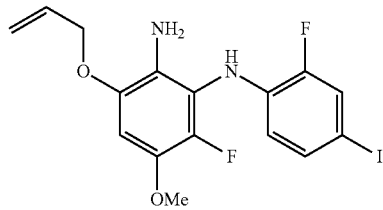 [SMILES: C=CCOc1cc(OC)c(F)c(Nc2ccc(I)cc2F)c1N]

To a solution of (3-allyloxy-5,6-difluoro-2-nitro-phenyl)-(2-fluoro-4-iodo-phenyl)-amine (Intermediate 7, 1.0 g, 2.22 mmol) in THF (8 mL) was drop wise added NaOMe solution [prepared by dissolving Na metal (51 mg, 2.2 mmol) in methanol (5 mL)] at −78° C. After complete addition, the reaction mixture was warmed to room temperature and stirred for 16 h. The progress of reaction was monitored by TLC. After completion, reaction mixture was concentrated under reduced pressure. The residue was dissolved in water and extracted with ethyl acetate (20 mL×3). The combined organic layer was washed with water (20 mL×2), dried over anhydrous sodium sulfate and concentrated to yield 3-allyloxy-6-fluoro-5-methoxy-2-nitro-phenyl)-(2-fluoro-4-iodo-phenyl)-amine (820 mg). A suspension of (3-allyloxy-6- fluoro-5-methoxy-2-nitro-phenyl)-(2-fluoro-4-iodo-phenyl)-amine (800 mg, 1.73 mmol) in ethanol (10 mL) was stirred at 70° C. to obtain a clear solution. To this hot solution, a freshly prepared solution of Na$_2$S$_2$O$_4$ (900 mg, 5.2 mmol) in water (1.8 mL) was added drop wise and stirred the reaction mixture at 90° C. for 1 h. The reaction mixture was concentrated under reduced pressure. The residue was dissolved in ethyl acetate, washed with water and brine. The combined organic layer was dried over anhydrous sodium sulfate and concentrated to yield 6-allyloxy-3-fluoro-N2-(2-fluoro-4-iodo-phenyl)-4-methoxy-benzene-1,2-diamine (720 mg). $^1$H-NMR (400 MHz, CDCl$_3$): δ3.74 (2H, bs), 3.83 (3H, s), 4.56 (2H, d, J=5.6), 5.32 (1H, d, J=10.8), 5.40-5.45 (2H, m), 6.04-6.09 (1H, m), 6.24 (1H, t), 6.52 (1H, d, J=7.6), 7.21 (1H, d, J=8.4), 7.36 (1H, d, J=10.4).

Intermediate 23

3-(Allyloxy)-5-fluoro-N1-(2-fluoro-4-iodophenyl)benzene-1,2-diamine

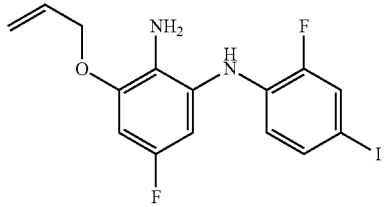

A suspension of N-(3-(allyloxy)-5-fluoro-2-nitrophenyl)-2-fluoro-4-iodobenzenamine (Intermediate 11, 1.56 g, 3.73 mmol) in ethanol (20 mL) was stirred at 70° C. to obtain a clear solution. To this hot solution was added dropwise a freshly prepared solution of Na$_2$S$_2$O$_4$ (1.94 g, 11.19 mmol) in water (3.5 mL) and stirred the reaction mixture at 90° C. for 1 h. The progress of reaction was monitored by TLC. After completion, the reaction mixture was concentrated under reduced pressure. The residue was dissolved in ethyl acetate, washed with water and concentrated to yield 3-(allyloxy)-5-fluoro-N1-(2-fluoro-4-iodophenyl)benzene-1,2-diamine (600 mg). $^1$H-NMR (400 MHz, CDCl$_3$): δ 3.65 (2H, bs), 4.57 (2H, d, J=5.6), 5.32 (1H, d), 5.40 (1H, s), 5.46 (1H, d), 6.03-6.10 (1H, m), 6.45 (1H, dd, J=10.4, 2.8), 6.52 (1H, dd), 6.59 (1H, t) 7.27 (1H, d, J=9.2), 7.38 (1H, dd, J=10.4, 2).

Intermediate 24

3,6-Difluoro-N1-(2-fluoro-4-iodophenyl)-5-methoxybenzene-1,2-diamine

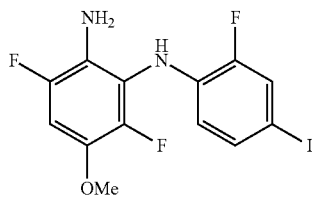

A suspension of 2,5-difluoro-N-(2-fluoro-4-iodophenyl)-3-methoxy-6-nitrobenzenamine (Intermediate 15, 565 mg, 1.3 mmol) in ethanol (12 mL) was stirred at 70° C. to obtain a clear solution. To this hot solution was dropwise added a freshly prepared solution of Na$_2$S$_2$O$_4$ (695 mg, 3.9 mmol) in water (2 mL) and stirred the reaction mixture at 90° C. for 1 h. The progress of reaction was monitored by TLC. After completion, the reaction mixture was concentrated and residue dissolved in ethyl acetate. The organic layer was washed with water, dried over anhydrous Na$_2$SO$_4$ and concentrated to yield 3,6-difluoro-N1-(2-fluoro-4-iodophenyl)-5-methoxy-benzene-1,2-diamine (320 mg). $^1$H-NMR (400 MHz, CDCl$_3$): δ 3.60 (2H, bs), 3.82 (3H, s), 5.41 (1H, bs), 6.23-6.27 (1H, m), 6.68-6.73 (1H, m), 7.23 (1H, s), 7.38 (1H, d, J=10.8).

Intermediate 25

N-2-(4-Bromo-2-fluoro-phenyl)-3,6-difluoro-4-methoxy-benzene-1,2-diamine

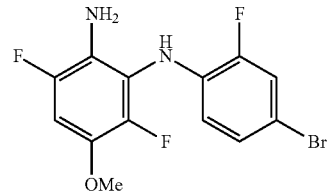

A suspension of (4-bromo-2-fluoro-phenyl)-(2,5-difluoro-3-methoxy-6-nitro-phenyl)-amine (Intermediate 16, 0.850 g, 2.2 mmol) in ethanol (13 mL) was stirred at 70° C. to obtain a clear solution. To this hot solution, was added a freshly prepared solution of Na$_2$S$_2$O$_4$ (1.2 g, 6.7 mmol) in water (2.4 mL) and stirred the reaction mixture at 90° C. for 1 h. The progress of reaction was monitored by TLC. After completion, the solvent was removed under reduced pressure. The residue was diluted with ethyl acetate, washed with water, and the organic phase was dried over anhydrous Na$_2$SO$_4$ and concentrated to yield N2-(4-bromo-2-fluoro-phenyl)-3,6-difluoro-4-methoxy-benzene-1,2-diamine as a brown solid (600 mg). $^1$H-NMR (400 MHz, CDCl$_3$): δ 3.61 (2H, bs), 3.82 (3H, s), 5.40 (1H, bs), 6.37 (1H, t), 6.68-6.73 (1H, m), 7.06 (1H, d, J=8.4), 7.24 (1H, d, J=14).

Intermediate 26

3-Fluoro-N1-(2-fluoro-4-iodophenyl)-5-methoxy-benzene-1,2-diamine

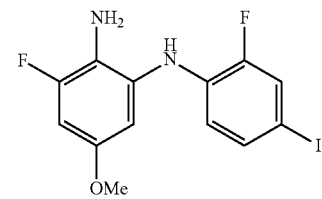

A suspension of 2-fluoro-N-(3,5-difluoro-2-nitrophenyl)-4-iodobenzenamine (Intermediate 17, 550 mg, 1.35 mmol) in ethanol (12 mL) was stirred at 70° C. to obtain a clear solution. To this hot solution was added dropwise a freshly prepared solution of Na$_2$S$_2$O$_4$ (707 mg, 4.0 mmol) in water (2 mL) and stirred the reaction mixture at 90° C. for 1 h. The progress of reaction was monitored by TLC. After completion, the reaction mixture was concentrated and residue dissolved in ethyl acetate. The organic layer was washed with water, dried over anhydrous sodium sulfate and concentrated to yield 3-fluoro-N1-(2-fluoro-4-iodophenyl)-5-methoxybenzene-1,2-diamine (448 mg). ¹H-NMR (400 MHz, CDCl₃): δ 3.86 (3H, s), 6.43-6.50 (2H, m), 6.56-6.61 (1H, m), 7.26-7.27 (1H, m), 7.37 (1H, d, J=10.0).

Intermediate 27

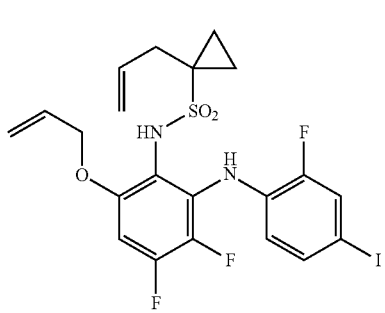 [SMILES: C=CCOc1cc(F)c(F)c(Nc2ccc(I)cc2F)c1NS(=O)(=O)C1(CC=C)CC1]

To a solution of 3-(allyloxy)-5,6-difluoro-N1-(2-fluoro-4-iodophenyl)benzene-1,2-diamine (Intermediate 18, 3.0 g, 7.1 mmol) in pyridine (30 mL) was added 1-allylcyclopropane-1-sulfonyl chloride (5.1 g, 28.6 mmol) and stirred the reaction mixture at 50° C. for 16 h. The progress of reaction was monitored by TLC. After completion, the volatiles were removed. The residue was dissolved in ethyl acetate, washed with 0.5 N aq HCl and water. The organic layer was dried over Na₂SO₄ and concentrated. The residue was purified by flash column chromatography to yield the desired compound (1.4 g). ¹H-NMR (400 MHz, CDCl₃): δ 0.78 (2H, m), 1.24 (2H, m), 2.70 (2H, d, J=7.2), 4.59 (2H, d, J=5.6), 5.03-5.11 (2H, m), 5.39-5.48 (2H, m), 5.62-5.70 (1H, m), 6.02-6.15 (1H, m), 6.07 (1H, s), 6.39-6.45 (1H, m), 6.51-6.55 (1H, m), 7.26 (1H, s), 7.35-7.39 (2H, m).

Intermediate 28

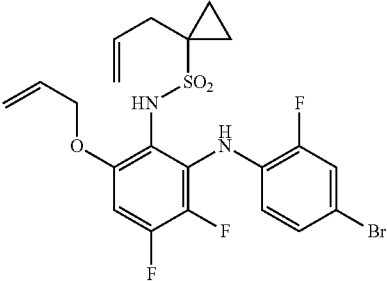 [SMILES: C=CCOc1cc(F)c(F)c(Nc2ccc(Br)cc2F)c1NS(=O)(=O)C1(CC=C)CC1]

To a solution of 3-(allyloxy)-N1-(4-bromo-2-fluorophenyl)-5,6-difluorobenzene-1,2-diamine (Intermediate 19, 500 g, 1.3 mmol) in pyridine (10 mL) was added 1-allylcyclopropane-1-sulfonyl chloride (968 mg, 5.4 mmol) and stirred the reaction mixture at 50° C. for 16 h. The progress of reaction was monitored by TLC. After completion, the reaction mixture was concentrated. The residue was dissolved in ethyl acetate, washed with 0.5 N aq HCl and water. The organic layer was dried over Na₂SO₄ and concentrated. The residue was purified by flash column chromatography to yield 105 mg of the desired compound. ¹H-NMR (400 MHz, CDCl₃): δ 0.78 (2H, m), 1.24 (2H, m), 2.71 (2H, d, J=7.2), 4.59 (2H, d, J=5.6), 5.06 (1H, d, J=18), 5.11 (1H, d, J=10), 5.41 (1H, d, J=10), 5.47 (1H, d, J=17.2), 5.66-5.68 (1H, m), 6.05-6.08 (2H, m), 6.51-6.56 (2H, m), 7.09 (1H, d, J=8.8), 7.21-7.28 (1H, m), 7.33 (1H, s).

Intermediate 29

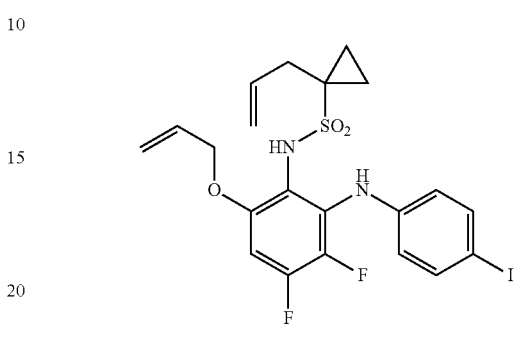

To a solution of 3-(allyloxy)-5,6-difluoro-N-1-(4-iodophenyl)benzene-1,2-diamine (Intermediate 20, 500 g, 1.2 mmol) in pyridine (10 mL) was added 1-allylcyclopropane-1-sulfonyl chloride (898 mg, 4.9 mmol) and stirred the reaction mixture at 50° C. for 16 h. The progress of reaction was monitored by TLC. After completion, the reaction mixture was concentrated under reduced pressure. The residue was dissolved in ethyl acetate, washed with 0.5 N aq HCl and water. The organic layer was dried over Na₂SO₄ and concentrated. The residue was purified by flash column chromatography to yield 115 mg of the desired compound. ¹H-NMR (400 MHz, CDCl₃): δ 0.79-0.76 (2H, m), 1.24-1.21 (2H, m), 2.69 (2H, d, J=7.2), 4.59 (2H, d, J=5.6), 5.05 (1H, d, J=17.2), 5.11 (1H, d, J=9.6), 5.41 (1H, d, J=10.8), 5.46 (1H, d, J=17.2), 5.65-5.67 (1H, m), 6.00-6.15 (1H, m), 6.07 (1H, s), 6.48-6.56 (3H, m), 7.32 (1H, s), 7.49 (2H, d, J=8.4).

Intermediate 30

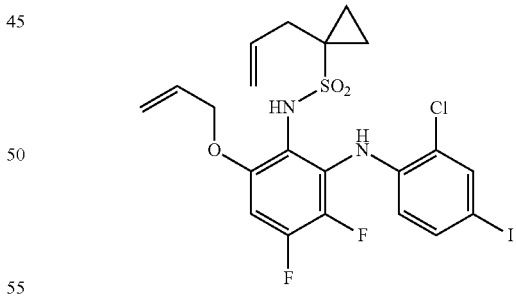

To a solution of 3-(allyloxy)-N1-(2-chloro-4-iodophenyl)-5,6-difluorobenzene-1,2-diamine (Intermediate 21, 500 g, 1.1 mmol) in pyridine (10 mL) was added 1-allylcyclopropane-1-sulfonyl chloride (827 mg, 4.6 mmol) and stirred the reaction mixture at 50° C. for 16 h. The progress of reaction was monitored by TLC. After completion, the reaction mixture was concentrated. The residue was dissolved in ethyl acetate, washed with 0.5 N aq HCl and water. The organic layer was dried over Na₂SO₄ and concentrated under reduced pressure. The residue was purified by flash column chromatography to yield the desired compound (90 mg). ¹H-NMR (400 MHz, CDCl$_3$): δ 0.78 (2H, m), 1.23 (2H, m), 2.71 (2H, d, J=7.6), 4.60 (2H, d, J=5.6), 5.04-5.11 (2H, m), 5.41 (1H, d, J=10.4), 5.47 (1H, d, J=17.2), 5.64-5.68 (1H, m), 6.03-6.15 (1H, m), 6.05 (1H, s), 6.31-6.34 (1H, m), 6.56-6.60 (1H, m), 7.35 (1H, d, J=8.8), 7.56 (1H, s), 7.63 (1H, d, J=5.2).

Intermediate 31

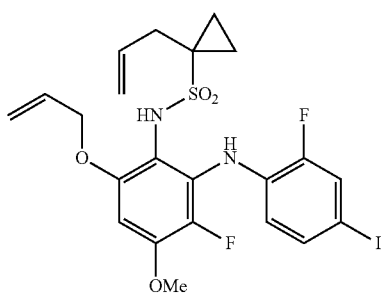 [SMILES: C=CCOc1cc(OC)c(F)c(Nc2ccc(I)cc2F)c1NS(=O)(=O)C1(CC=C)CC1]

To a solution of 3-(allyloxy)-6-fluoro-N1-(2-fluoro-4-iodophenyl)-5-methoxybenzene-1,2-diamine (Intermediate 22, 800 mg, 1.85 mmol) in pyridine (20 mL) was added 1-allylcyclopropane-1-sulfonyl chloride (669 mg, 3.7 mmol) and stirred the reaction mixture at room temperature for 24 h. The progress of reaction was monitored by TLC. After completion, the reaction mixture was concentrated. The residue was dissolved in ethyl acetate, washed with 0.5 N aq HCl and water. The organic layer was dried over Na$_2$SO$_4$ and concentrated under reduced pressure. The residue was purified by flash column chromatography to yield the desired compound (400 mg). $^1$H-NMR (400 MHz, CDCl$_3$): δ 0.76 (2H, m), 1.22 (2H, m), 2.71 (2H, d, J=7.2), 3.91 (3H, s), 4.62 (2H, d, J=5.2), 5.03-5.10 (2H, m), 5.39 (1H, d, J=10.4), 5.46 (1H, d, J=17.2), 5.63-5.68 (1H, m), 5.98 (1H, s), 6.05-6.09 (1H, m), 6.35-6.40 (2H, m), 7.20-7.26 (2H, m), 7.33-7.37 (1H, dd, J=2, 10.8).

Intermediate 32

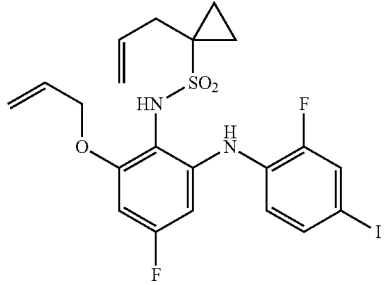 [SMILES: C=CCOc1cc(F)cc(Nc2ccc(I)cc2F)c1NS(=O)(=O)C1(CC=C)CC1]

To a solution of 3-(allyloxy)-5-fluoro-N1-(2-fluoro-4-iodophenyl)benzene-1,2-diamine (Intermediate 23, 600 mg, 1.5 mmol) in pyridine (20 mL) was added 1-allylcyclopropane-1-sulfonyl chloride (1.1 g, 6.0 mmol) and stirred the reaction mixture at 50° C. for 16 h. The progress of reaction was monitored by TLC. After completion, the reaction mixture was concentrated. The residue was dissolved in ethyl acetate, washed with 0.5 N aq HCl and water. The organic layer was dried over Na$_2$SO$_4$ and concentrated under reduced pressure. The residue was purified by flash column chroma-tography to yield the desired compound (289 mg). $^1$H-NMR (400 MHz, CDCl$_3$): δ 0.77 (2H, m), 1.24 (2H, m), 2.73 (2H, d, J=7.6), 4.58 (2H, d), 5.03-5.11 (2H, m), 5.34-5.47 (2H, m), 5.65-5.69 (1H, m), 5.98 (1H, s), 6.04 (1H, m), 6.52 (1H, t, J=10.4), 7.32-7.36 (1H, m), 7.40-7.44 (2H, m).

Intermediate 33

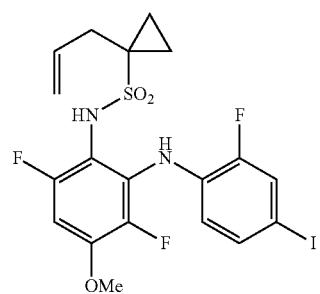 [SMILES: C=CCC1(S(=O)(=O)Nc2c(F)cc(OC)c(F)c2Nc2ccc(I)cc2F)CC1]

To a solution of 3,6-difluoro-N1-(2-fluoro-4-iodophenyl)-5-methoxybenzene-1,2-diamine (Intermediate 24, 320 mg, 0.81 mmol) in pyridine (15 mL) was added 1-allylcyclopropane-1-sulfonyl chloride (880 mg, 4.87 mmol) and stirred the reaction mixture at 50° C. for 16 h. The progress of reaction was monitored by TLC. After completion, the reaction mixture was concentrated. The residue was dissolved in ethyl acetate, washed with 0.5 N aq HCl and water. The organic layer was dried over Na$_2$SO$_4$ and concentrated. The residue was purified by flash column chromatography to yield the desired compound (33 mg). $^1$H-NMR (400 MHz, CDCl$_3$): δ 0.82-0.89 (2H, m), 1.20-1.29 (2H, m), 2.76 (2H, d, J=7.2), 3.87-3.92 (3H, m), 5.15 (2H, d, J=11.6), 5.71-5.78 (1H, m), 5.90 (1H, s), 6.37-6.43 (1H, m), 6.53-6.58 (1H, m), 6.94 (1H, s), 7.25 (1H, d, J=7.2), 7.37 (1H, dd, J=10.8, 1.6).

Intermediate 34

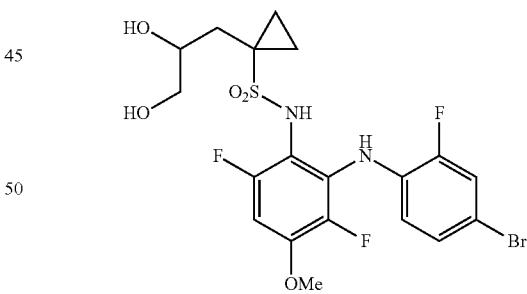

To a solution of N2-(4-bromo-2-fluorophenyl)-3,6-difluoro-4-methoxybenzene-1,2-diamine (Intermediate 25, 500 mg, 1.44 mmol) in pyridine (10 mL) was added 1-allylcyclopropane-1-sulfonyl chloride (1.04 g, 5.76 mmol) and stirred the reaction mixture at 50° C. for 16 h. The progress of reaction was monitored by TLC. After completion, the reaction mixture was concentrated. The residue was dissolved in ethyl acetate, washed with 0.5 N aq HCl and water. The organic layer was dried over Na$_2$SO$_4$ and concentrated. The residue was purified by flash column chromatography to yield the desired compound (35 mg). $^1$H-NMR (400 MHz, CDCl$_3$): δ 0.83 (2H, m), 1.20 (2H, m), 2.76 (2H, d, J=6.8), 3.90 (3H, s), 5.14 (2H, d, J=12.8 Hz), 5.70-5.74 (1H, m), 5.98 (1H, s), 6.54 (2H, m), 6.92 (1H, s), 7.07 (1H, d, J=8.0), 7.21 (1H, d, J=10.4).

Intermediate 35

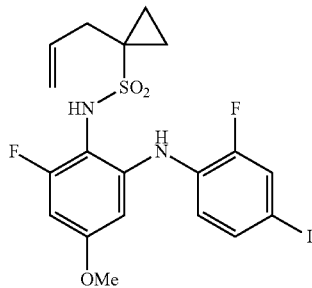 [SMILES: C=CCC1(S(=O)(=O)Nc2c(F)cc(OC)cc2Nc2ccc(I)cc2F)CC1]

To a solution of 3-fluoro-N1-(2-fluoro-4-iodophenyl)-5-methoxybenzene-1,2-diamine (Intermediate 26, 488 mg, 1.3 mmol) in pyridine (20 mL) was added 1-allylcyclopropane-1-sulfonyl chloride (1.0 g, 5.2 mmol) and stirred the reaction mixture at 50° C. for 16 h. The progress of reaction was monitored by TLC. After completion, the reaction mixture was concentrated under reduced pressure. The residue was dissolved in ethyl acetate, washed with 0.5 N aq HCl and water. The organic layer was dried over $Na_2SO_4$ and concentrated. The residue was purified by flash column chromatography to yield the desired compound (60 mg). $^1$H-NMR (400 MHz, $CDCl_3$): δ 0.76 (2H, m), 1.23 (2H, m), 2.77 (2H, d, J=7.6), 3.88 (3H, s), 5.06-5.13 (2H, m), 5.67-5.71 (1H, m), 5.94 (1H, s), 6.23 (1H, dd, J=2.4, 9.6), 6.50 (1H, dd, J=2.8, 10.8), 7.01 (1H, t), 7.35 (1H, d, J=8.8), 7.40-7.44 (2H, m).

Intermediate 36

Preparation of 1-Allyl-N-(3,4-difluoro-2-(2-fluoro-4-iodophenyamino)-6-allyloxyphenyl)cyclopropane-1-sulfonamide

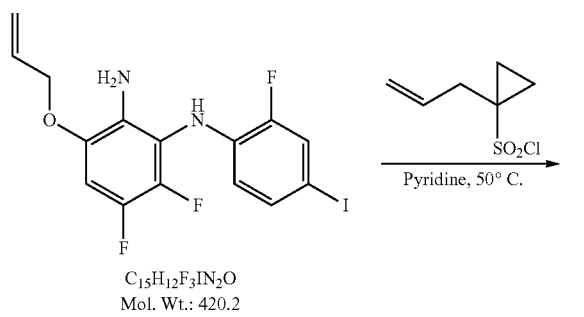

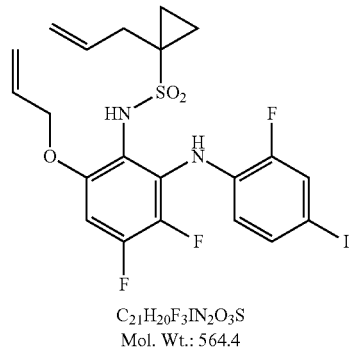

3-(Allyloxy)-5,6-difluoro-N-(2-fluoro-4-iodophenyl)benzene-1,2-diamine (Intermediate 18, 420.2 mg, 1.0 mmol) is dissolved in anhydrous pyridine (1.0 mL), and to this solution is added 1-allyl-cyclopropyl-1-sulfonyl chloride (250.0 mg, 1.38 mmol, freshly prepared) at room temperature. The mixture is heated in an oil bath under nitrogen for 48 h. The TLC analysis of mixture indicated that a new polar spot is formed when compared with starting material. The reaction mixture is diluted with ethyl acetate and washed with 0.01 M HCl, water, and brine. The organic layer is dried over $MgSO_4$ and concentrated under reduced pressure. Flash chromatography of crude material over silica gel using 30 to 40% hexanes:ethyl acetate affords pure compound (375 mg, 66%) MS analysis: $[M+H]^+$565; $^1$H NMR (400 MHz, $CDCl_3$): 0.81 (t, J=6.0 Hz, 2H, Cylopropyl-$CH_2$), 1.26 (t, J=6.0 Hz, 2H, Cylopropyl-$CH_2$), 2.73 (d, J=8.0 Hz, 2H, —$CH_2$), 4.62 (dt, J=1.2, 5.2 Hz, 2H, $OCH_2$), 5.08 (dd, J=1.2, 16.0 Hz, 1H, =$CH_2$), 5.13 (dt, J=1.6, 8.0 Hz, 1H, =$CH_2$), 5.44 (dd, J=1.6, 8.0 Hz, 1H, =$CH_2$) 5.51 (dt, J=1.6, 8.0 Hz, 1H, =$CH_2$), 5.69 (m, 1H, =CH), 6.07 (m, 1H, =CH), 6.12 (1H, s, NH), 6.44 (m, 1H, ArH), 6.56 (dd, J=4.0, 12.0 Hz, 1H, ArH), 7.28 (d, J=8.0 Hz, 1H, ArH), 7.40 (dd, J=1.0, 8.0 Hz, 2H, ArH).

Example 1

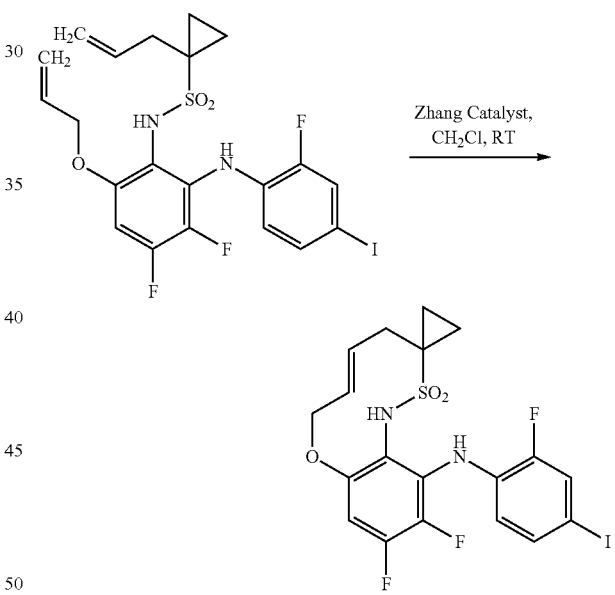

Method A.

A diluted solution of Zhang catalyst [prepared as described in *Tetrahedron Letters* 46 (2005) 7225-7228, compound 8], (1.5 mg/mL, 50 µL) in $CH_2Cl_2$ was added to a $CH_2Cl_2$ solution (1.0 mL) of Intermediate 27 (6.3 mg, 0.011 mmol) at room temperature and the mixture was stirred at room temperature for an additional 24 h. The mixture was then concentrated and purified by preparative TLC (silica gel) developing with hexanes:ethyl acetate, and the band corresponding to a new compound was collected and eluted with acetone. The TLC-homogenous pure Example 1 was isolated as a solid (4.8 mg, 80%). MS analysis: $[m+H]^+$ 537; $^1$H NMR (400 MHz, $CDCl_3$): 0.74 (brs s, $CH_2$), 1.14 (brs, $CH_2$), 3.14 (m, 2H, $CH_2$), 4.92 (s, 2H, $OCH_2$), 5.46 (dd, J=12.0 Hz, 1H, =CH), 5.72 (dd, J=8.0, 12.0 Hz, 1H, =CH), 6.27 (s, 1H, NH), 6.51 (m, 2H, ArH), 7.18 (s, 1H, NH), 7.29 (d, J=8.0, 1H, ArH), 7.41 (d, J=12.0 Hz, 1H, ArH).

Method B.

To a degassed solution of bis-olefin (Intermediate 27, 930 mg, 1.64 mmol) in dichloroethane (60 mL), Hoveyda-Grubbs 2nd generation catalyst (120 mg, 0.19 mmol, 10 mol %) was added. The reaction mixture was stirred at 70° C. for 3 h. The progress of reaction was monitored by TLC. After completion, the reaction mixture was concentrated under reduced pressure. The residue was purified by flash column chromatography to yield the desired compound (225 mg).

Example 2

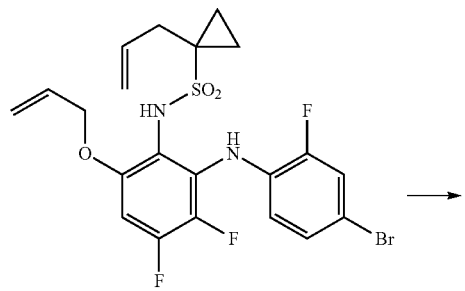

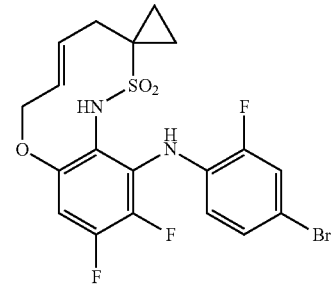

To a degassed solution of bis olefin (Intermediate 28, 100 mg, 0.204 mmol) in dichloroethane (15 mL), Hoveyda-Grubbs 2nd generation catalyst [(1,3-Bis-(2,4,6-trimethylphenyl)-2-imidazolidinylidene)dichloro(o-isopropoxyphenylmethylene)ruthenium, CAS #301224-40-8, 13 mg, 0.02 mmol, 10 mol %] was added. The reaction mixture was stirred at 70° C. for 3 h. The progress of reaction was monitored by TLC. After completion, reaction mixture was concentrated under reduced pressure. The residue was purified by flash column chromatography to yield the desired compound (30 mg). $^1$H-NMR (400 MHz, CDCl$_3$): δ 0.72 (2H, m), 1.12 (2H, m), 3.13 (2H, d), 4.89 (2H, d), 5.41-5.44 (1H, m), 5.68-5.71 (1H, m), 6.25 (1H, s), 6.47-6.51 (1H, m), 6.58-6.62 (1H, m), 7.06-7.12 (2H, m), 7.21-7.26 (1H, m).

Example 3

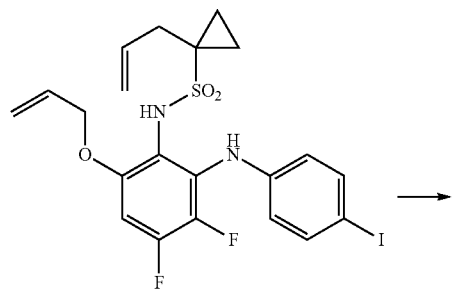

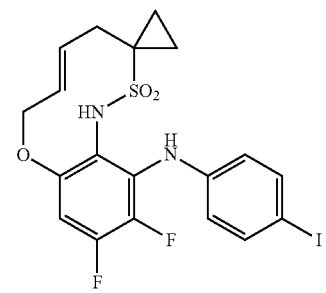

To a degassed solution of bis olefin (Intermediate 29, 110 mg, 0.212 mmol) in dichloroethane (20 mL), Hoveyda-Grubbs 2nd generation catalyst (14 mg, 0.02 mmol, 10 mol %) was added. The reaction mixture was stirred at 70° C. for 3 h. The progress of reaction was monitored by TLC. After completion, the reaction mixture was concentrated under reduced pressure. The residue was purified by flash column chromatography to yield the desired compound (35 mg). $^1$H-NMR (400 MHz, CDCl$_3$): δ 0.72 (2H, m), 1.11 (2H, m), 3.13 (2H, d, J=7.2), 4.88 (2H, s), 5.41-5.46 (1H, m), 5.68-5.72 (1H, m), 6.22 (1H, s), 6.44-6.48 (1H, m), 6.59 (2H, dd, J=2.8, 8.4), 7.07 (1H, s), 7.50 (2H, d, J=8.8).

Example 4

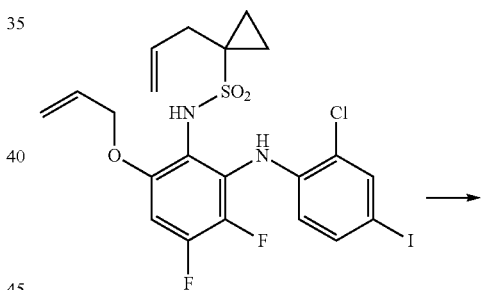

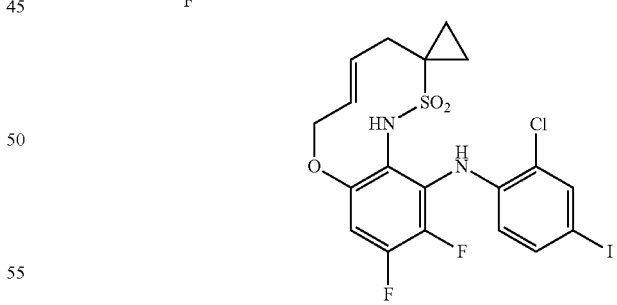

To a degassed solution of bis-olefin (Intermediate 30, 170 mg, 0.29 mmol) in dichloroethane (40 mL), Hoveyda-Grubbs 2nd generation catalyst (40 mg, 0.058 mmol) was added. The reaction mixture was stirred at 70° C. for 3 h. The progress of the reaction was monitored by TLC. After completion, the reaction mixture was concentrated under reduced pressure. The residue was purified by flash column chromatography to yield the desired compound (70 mg). $^1$H-NMR (400 MHz, CDCl$_3$): δ 0.72 (2H, m), 1.13 (2H, m), 3.14 (2H, d), 4.90 (2H, s), 5.43-5.45 (1H, m), 5.68-5.71 (1H, m), 6.25 (1H, s), 6.37-6.40 (1H, m), 6.54-6.57 (1H, m), 7.36-7.39 (2H, m), 7.64 (1H, s).

Example 5

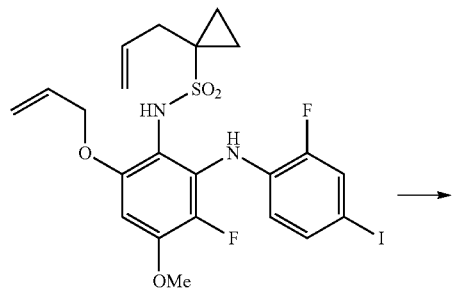

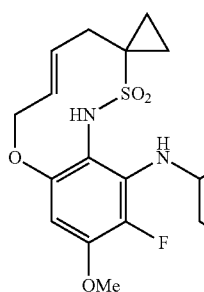

To a degassed solution of bis-olefin (Intermediate 31, 515 mg, 0.89 mmol) in dichloroethane (50 mL), Hoveyda-Grubbs 2nd generation catalyst (90 mg, 0.14 mmol, 16 mol %) was added. The reaction mixture was stirred at 70° C. for 3 h. The progress of reaction was monitored by TLC. After completion, the reaction mixture was concentrated under reduced pressure. The residue was purified by flash column chromatography to yield the desired compound (100 mg). $^1$H-NMR (400 MHz, CDCl$_3$): δ 0.70 (2H, m), 1.12 (2H, m), 3.13 (2H, d, J=7.2), 3.92 (3H, s), 4.91 (2H, s), 5.42-5.45 (1H, m), 5.68-5.70 (1H, m), 6.16 (1H, s), 6.30 (1H, d, J=7.2), 6.42-6.44 (1H, m), 7.01 (1H, s), 7.22 (1H, s), 7.35 (1H, d, J=10.8).

Example 6

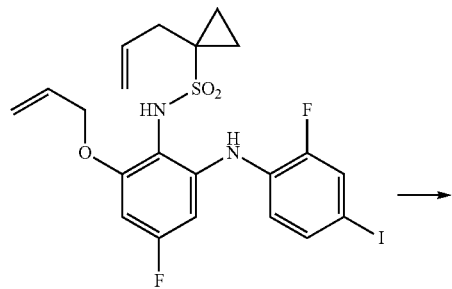

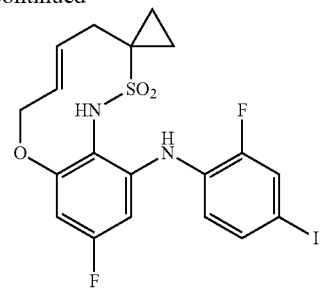

To degassed solution of bis-olefin (Intermediate 32, 290 mg, 0.53 mmol) in dichloroethane (40 mL), Hoveyda-Grubbs 2nd generation catalyst (40 mg, 0.064 mmol, 12 mol %) was added and stirred the reaction mixture at 70° C. for 3 h. The progress of reaction was monitored by TLC. After completion, the reaction mixture was concentrated under reduced pressure. The residue was purified by flash column chromatography to yield the desired compound (50 mg).

Example 7

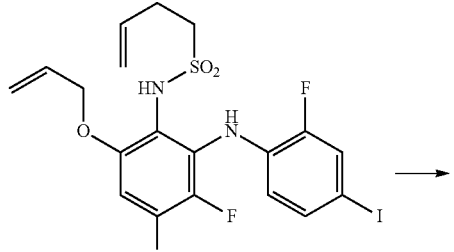

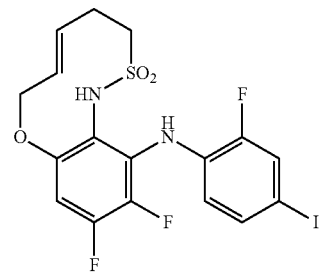

To a solution of bis-olefin (Intermediate 36, 650 mg, 1.20 mmol) in dichloroethane (40 mL), Hoveyda-Grubbs 2nd generation catalyst (100 mg, 0.15 mmol, 13 mol %) was added and reaction mixture stirred at 70° C. for 2 h. The progress of reaction was monitored by TLC. After completion, the reaction mixture was concentrated and the residue was purified by flash column chromatography to yield the desired compound (60 mg).

Example 8

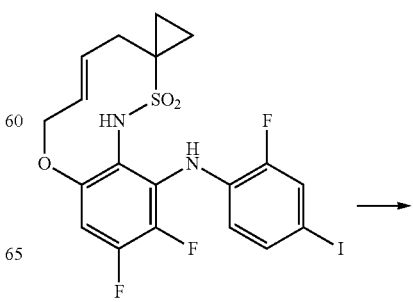

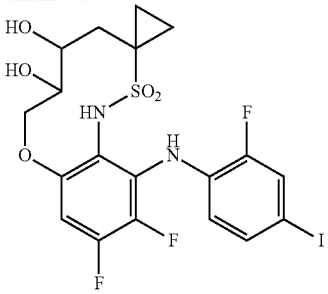

To a THF solution (0.5 mL) of the compound prepared in Example 1 (4.8 mg, 0.009 mmol) is added NMO (5.0 mg) followed by OsO$_4$ as a solution (5.0 μL, 4% wt in water), via syringe at room temperature. The mixture is stirred over night (14 h). Starting material is completely consumed by TLC analysis to form a highly polar product (50% hexanes:ethyl acetate). The mixture is diluted with ethyl acetate (5.0 mL), washed with Na$_2$S$_2$O$_3$ (1% solution, 2.0 mL), water, and finally with brine. The organic layer is separated, dried over MgSO$_4$ and evaporated. The crude compound is purified by preparative TLC, and the most polar band moved by ethyl acetate is collected. Extraction of the collected silica band by acetone yields racemic diol product (3.8 mg, 74%). MS analysis: [M+H]$^+$ 571; $^1$H NMR (400 MHz, CDCl$_3$): 0.68 (brs s, 2H, CH$_2$), 0.75 (m, 1H), 1.17 (brs, 1H, CH$_2$), 2.07 (s, 2H, CH$_2$), 2.12 (s, 2H, CH$_2$), 3.10-2.50 (m, 3H), 3.65 (m, 1H), 3.85 (d, 1H), 4.04 (brs, 1H), 4.42 (brt, 1H), 6.40 (m, 1H), 6.88 (s, 1H, ArH), 7.28 (d, 1H, ArH), 7.30 (d, J=8.0, 1H, ArH).

Example 8a 8a is obtained from the mixture of stereoisomers 8 by chiral HPLC separation to afford the single stereoisomer 8a. HPLC conditions for separating 8a and 8b: Hexane:Ethanol (90:10 v/v); Column: Chiralcel OD-H (250×4.6 mm) 5 uM; Flow Rate: 1.5 ml/min, Temperature: Ambient; Concentration: 1.0 mg/ml, UV Detection: 220 nm. Compound 8a elutes at 15.4 min. MS analysis: [M+H]$^+$571.05.

Example 8b 8b is obtained from the mixture of stereoisomers 8 by chiral HPLC separation to afford the single stereoisomer 8b. HPLC conditions for separating 8a and 8b: Hexane:Ethanol (90:10 v/v); Column: Chiralcel OD-H (250×4.6 mm) 5 uM; Flow Rate: 1.5 ml/min, Temperature: Ambient; Concentration: 1.0 mg/ml, UV Detection: 220 nm. Compound 8a elutes at 19.5 min. MS analysis: [M+H]$^+$571.00.

Example 9

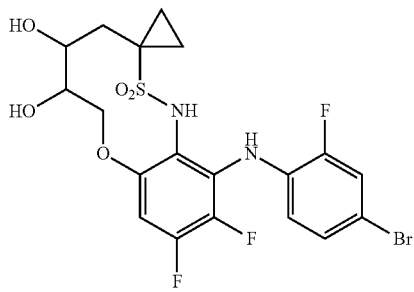 [SMILES: O=S1(=O)Nc2c(cc(F)c(F)c2Nc2ccc(Br)cc2F)OCC(O)C(O)CC12CC2]

To a solution of metathesis product prepared in Example 2 (37 mg, 0.075 mmol) in THF (2 mL) were added NMO (11 mg, 0.094 mmol) and OsO$_4$ solution (0.05 mL, 0.0075 mmol, 4% in water) at room temperature. The reaction mixture was stirred at room temperature for 16 h. The progress of reaction was monitored by TLC. After completion, the reaction mixture was concentrated under reduced pressure and residue purified by reverse phase HPLC to yield the desired compound (4 mg). $^1$H-NMR (400 MHz, CDCl$_3$): δ 7.24 (d, 1H), 7.15 (d, 1H), 6.98 (s, 1H), 6.5 (m, 1H), 4.5 (bs, 1H), 4.08 (bs, 1H), 3.68 (bs, 2H), 3.5 (m, 1H), 3.22 (bs, 1H), 2.5 (bs, 2H), 2.3 (bs, 2H), 2.13 (m, 1H), 2.07 (s, 1H), 0.75 (m, 2H). MS: m/z 523.2 and 525.2 (1:1) [M+H]$^+$.

Example 10

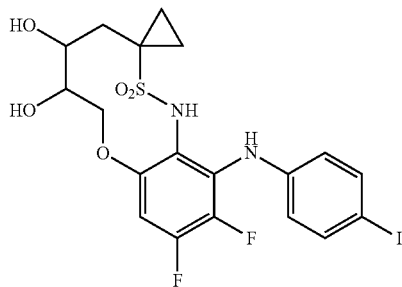 [SMILES: O=S1(=O)Nc2c(cc(F)c(F)c2Nc2ccc(I)cc2)OCC(O)C(O)CC12CC2]

To a solution of metathesis product prepared in Example 3 (35 mg, 0.068 mmol) in THF (2 mL) were added NMO (11 mg, 0.089 mmol) and OsO$_4$ solution (0.05 mL, 0.0068 mmol, 4% in water) at room temperature. The reaction mixture was stirred at room temperature for 16 h. The progress of reaction was monitored by TLC. After completion, reaction mixture was concentrated under reduced pressure and residue purified by reverse phase HPLC to yield the desired compound as off-white solid (13 mg). $^1$H-NMR (400 MHz, CDCl$_3$): δ 7.5 (d, 2H), 6.87 (s, 1H), 6.58 (d, 2H), 4.42 (bs, 1H), 4.1 (bs, 1H), 3.81 (d, 1H), 3.65 (m, 1H), 3.4 (m, 3H), 2.58 (bs, 2H), 2.38 (s, 1H), 2.18 (d, 1H), 0.65-0.82 (m, 3H). MS: m/z 553.0 [M+H]$^+$.

Example 11

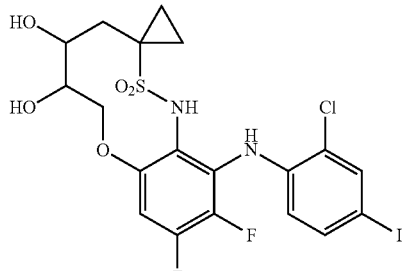

To a solution of metathesis product prepared in Example 4 (70 mg, 0.13 mmol) in THF (4 mL) were added NMO (60 mg, 0.5 mmol) and OsO$_4$ solution (0.1 mL, 0.013 mmol, 4% in water) at room temperature. The reaction mixture was stirred at room temperature for 16 h. The progress of reaction was monitored by TLC. After completion, the reaction mixture was concentrated and residue purified by reverse phase HPLC to yield the desired compound (25 mg). ¹H-NMR (400 MHz, CD₃OD): δ 7.62 (s, 1H), 7.4 (d, 1H), 6.9 (m, 1H), 6.4 (m, 1H), 4.4 (bt, 2H), 4.08 (d, 1H), 4.0 (bs, 1H), 2.8 (bs, 4H), 1.8-2.07 (m, 2H), 0.97 (m, 1H), 0.9 (m, 1H), 0.78 (m, 2H).

Example 12

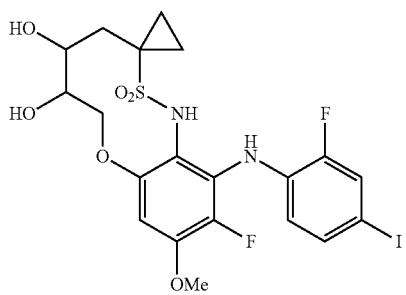

To a solution of metathesis product prepared in Example 5 (43 mg, 0.078 mmol) in THF (4 mL) were added NMO (40 mg, 0.34 mmol) and OsO₄ solution (0.06 mL, 0.0078 mmol, 4% in water) at room temperature. The reaction mixture was stirred at room temperature for 16 h. The progress of reaction was monitored by TLC. After completion, the reaction mixture was concentrated and residue purified by reverse phase HPLC to yield the desired compound (15 mg). ¹H-NMR (400 MHz, CDCl₃): δ 7.38 (d, 1H), 7.21 (d, 1H), 6.97 (s, 1H), 6.4 (m, 1H), 4.5 (bs, 2H), 4.02-4.17 (m, 2H), 3.8 (s, 3H), 3.6 (bs, 2H), 3.1 (bs, 1H), 2.75 (bs, 1H), 2.18 (d, 2H), 0.9 (bs, 2H), 0.75 (bs, 2H).

Example 13

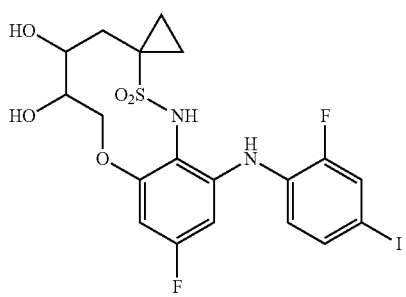

To a solution of metathesis product prepared in Example 6 (50 mg, 0.1 mmol) in THF (3 mL) were added NMO (50 mg, 0.4 mmol) and OsO₄ solution (0.06 mL, 0.01 mmol, 4% in water) at room temperature. The reaction mixture was stirred at room temperature for 16 h. The progress of reaction was monitored by TLC. After completion, the reaction mixture was concentrated under reduced pressure and residue purified by reverse phase HPLC to yield the desired compound (2 mg). ¹H-NMR (400 MHz, CD₃OD): δ 7.5 (d, 1H), 7.4 (d, 1H), 7.1 (t, 1H), 6.42 (d, 1H), 6.39 (d, 1H), 4.6 (s, 1H), 4.4 (bs, 1H), 4.0 (m, 2H), 1.9-2.03 (d, 2H), 0.96 (bs, 2H), 0.7 (bs, 2H). MS: m/z 553.3 [M+H]⁺.

Example 14

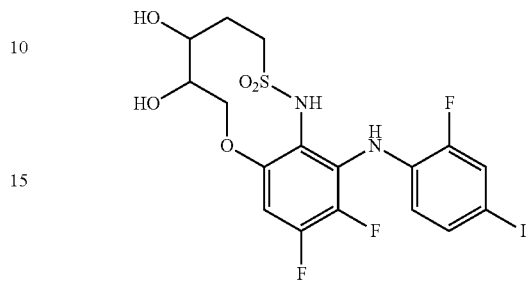

To a solution of metathesis product prepared in Example 7 (60 mg, 0.1 mmol) in THF (3 mL) were added NMO (60 mg, 0.5 mmol) and OsO₄ solution (0.07 mL, 0.01 mmol, 4% in water), and stirred the reaction mixture at room temperature for 16 h. The progress of reaction was monitored by TLC. After completion, the reaction mixture was concentrated under reduced pressure and residue obtained wad purified by reverse phase HPLC to yield the desired compound (6 mg). ¹H-NMR (400 MHz, CD₃OD): δ 7.41 (d, 1H), 7.3 (d, 1H), 6.95 (m, 1H), 6.5 (m, 1H), 4.6 (s, 1H), 4.4 (bs, 1H), 4.2 (d, 1H), 3.94 (d, 1H), 3.2 (m, 1H), 2.87 (m, 1H), 2.5 (bs, 1H), 2.1 (bs, 1H). MS: m/z 545.4 [M+H]⁺.

Example 15

Preparation of N-(3,6-Difluoro-2,2-fluoro-4-iodophenylamino)-4-methoxyphenyl)-1-(2,3-dihydroxypropyl(cyclopropane-1-sulfonamide Step 1: Synthesis of 2-fluoro-N-(2,3,5-trifluoro-6-nitrophenyl)-4-iodobenzeneamine

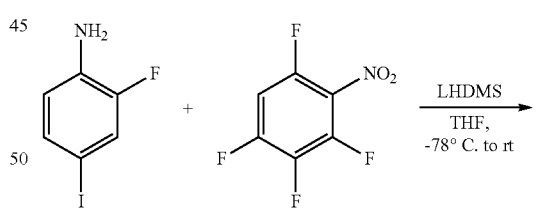

A solution of 4-iodo-2-fluoro aniline (3.64 g, 15.37 mmol) in dry THF (100 mL) was cooled to −78° C. in a dry iceacetone bath under a nitrogen atmosphere. To this solution was added dropwise via syringe a 1 M solution of LHDMS in THF (15.4 mL). During the addition the solution turns green and the mixture was stirred at that temperature for an additional 1 h. The mixture was cooled and to it was then added dropwise a solution of 1,2,3,5-tetrafluoro-4-nitrobenzene (3 g, 15.37 mmol) in dry THF (10.0 mL) via syringe. During the addition the color of the mixture changes to dark purple. The mixture was then allowed to stir at −78° C. for 1 h and then warmed to room temperature and stirred overnight (12 h). The mixture was then concentrated under vacuo to remove ⅔ of the THF, diluted with ethyl acetate (100 mL), washed with water (2×50 mL), and finally with brine. The organic layer was dried over MgSO$_4$ and evaporated under reduced pressure. The crude material was purified by careful flash column chromatography over silica gel using a 1-5% ethyl acetate/hexanes gradient to afford the desired product as a yellow solid (4.4 g, 70%). $^1$H NMR (400 MHz, DMSO-d$_6$): 6.85 (t, 1H), 7.35 (d, 1H), 7.60-7.65 (m, 2H), 8.78 (s, 1H).

Step 2: Synthesis of 2-fluoro-N-(2,5-difluoro-3-methoxy-6-nitrophenyl)-4-iodobenzeneamine

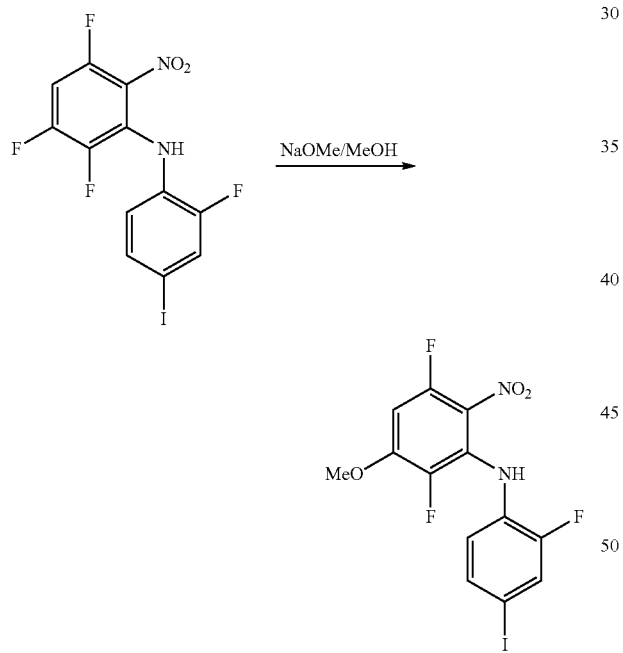

To a solution of 2-fluoro-N-(2,3,5-trifluoro-6-nitrophenyl)-4-iodobenzeneamine (2.55 g, 6.16 mmol) in THF (40 mL), was slowly added NaOMe solution (25% in MeOH, 1.4 mL, 0.62 mmol) at −78° C. The mixture becomes dark in color immediately. After the addition was complete, the reaction mixture was warmed to rt and stirred overnight. It was then diluted with ethyl acetate and washed with water, brine and then dried. After removal of volatiles, the crude product was purified by silica gel flash column using 2-10% ethyl acetate/hexanes as eluent to produce the desired product as yellow powder (1.2 g, 48%). Unreacted starting material 2-fluoro-N-(2,3,5-trifluoro-6-nitrophenyl)-4-iodobenzeneamine (1 g) was also recovered.

Step 3: Synthesis of 3,6-difluoro-N$^1$-(2-fluoro-4-iodophenyl)-5-methoxybenzene-1,2-diamine

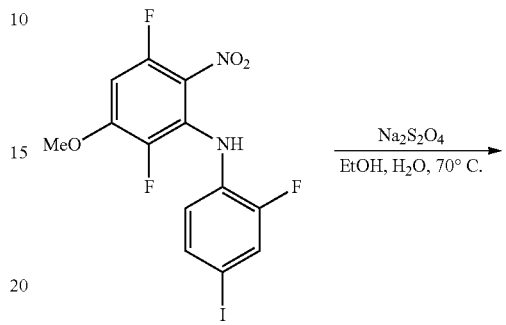

A suspension of 2-fluoro-N-(2,5-difluoro-3-methoxy-6-nitrophenyl)-4-iodobenzeneamine (12.5 g, 29.5 mmol) in EtOH (200 mL) was heated at 70° C. to form a clear transparent solution and to this hot solution was added dropwise a freshly prepared solution of Na$_2$S$_2$O$_4$ in water (15 g, 86 mmol, in 30 mL). The mixture was further heated for 1 h at 90° C. Upon cooling to room temperature the mixture was concentrated to remove ethanol under reduced pressure. The residue was diluted with ethyl acetate (25 mL), washed with water and brine, The organic layer was separated, dried over MgSO$_4$ and concentrated under reduced pressure to yield off white solid (10.2 g, 88%). The solid was used as was in the next reaction without purification.

Step 4: Synthesis of 1-allyl-N-(3,6-difluoro-2-(2-fluoro-4-iodophenylamino)-4-methoxyphenyl)cyclopropane-1-sulfonamide

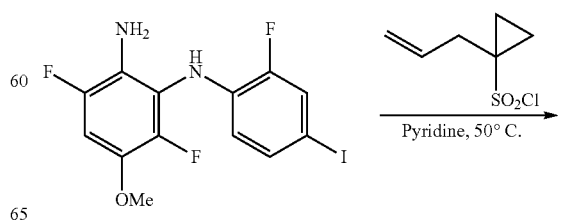

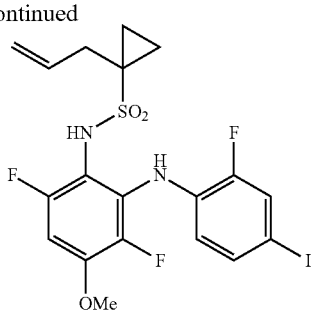

3,6-Difluoro-N[1]-(2-fluoro-4-iodophenyl)-5-methoxybenzene-1,2-diamine (10 g, 25.3 mmol) was dissolved in anhydrous pyridine (50 mL) and to this solution was added sulfonyl chloride (6.5 g, 50.6 mmol, freshly purified) at room temperature. The mixture was heated in an oil bath at 45° C. under nitrogen for 72 h. The TLC analysis of mixture indicates the formation of a new polar spot and disappearance of the starting material. The solvents were evaporated and the desired product was obtained from the crude mixture after silica gel chromatography using 10% ethyl acetate/hexanes as eluent. Yield (6.5 g, 48%) $^1$H NMR (400 MHz, CDCl$_3$): 0.81 (m, 2H), 1.21 (m, 2H), 2.73 (d, 2H), 3.88 (s, 3H), 5.11 (d, 2H), 5.75 (m, 1H), 5.8 (s, 1H), 6.4 (t, 1H), 6.51 (m, 1H), 6.8 (s, 1H), 7.2 (s, 1H), 7.33 (m, 1H).

Step 5: Synthesis of N-(3,6-difluoro-2-(2-fluoro-4-iodophenylamino)-4-methoxyphenyl)-1-(2,3-dihydroxypropyl)cyclopropane-1-sulfonamide

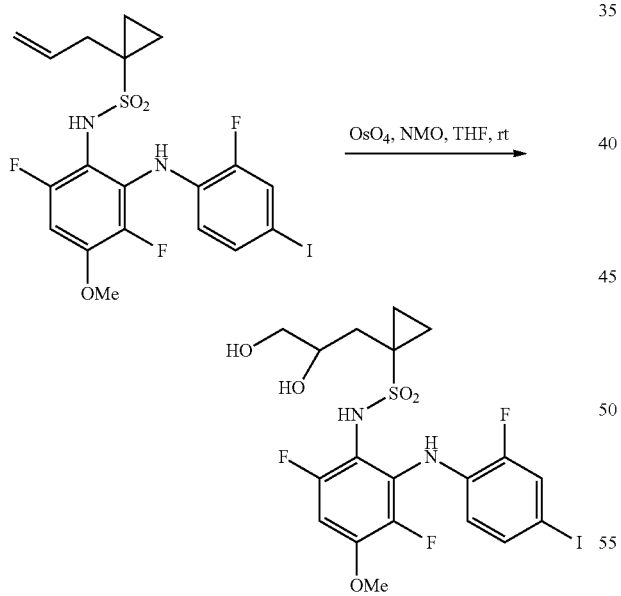

Method A.

To a solution of 1-allyl-N-(3,6-difluoro-2-(2-fluoro-4-iodophenylamino)-4-methoxyphenyl)cyclopropane-1-sulfonamide (3.4 g, 6.3 mmol) in THF (100 mL) was added N-methyl morpholine (0.85 g, 6.3 mmol) followed by OsO$_4$ as a solution (4 mL, 4% wt in water, 0.63 mmol) by syringe at room temperature. The mixture was stirred over night (14 h). Starting material was completely consumed, as indicated by TLC analysis, and a more polar product was formed (baseline in 50% hexanes:ethyl acetate). The mixture was diluted with ethyl acetate and washed with Na$_2$S$_2$O$_3$ (1% solution), water, and finally with brine. The organic layer was separated, dried over MgSO$_4$ and evaporated. The crude compound was purified by flash silica gel chromatography using 8-100% ethyl acetate/hexanes. Yield (2.5 g, 69%) $^1$H NMR (400 MHz, CDCl$_3$): 0.90 (br s, 2H), 1.20-1.22 (m, 2H), 1.28 (m, 1H), 1.45 (m, 1H), 1.75 (m, 1H), 2.45-2.48 (m, 1H), 3.48 (m, 1H), 3.62 (m, 1H), 3.80 (s, 3H), 4.06 (m, 1H), 6.40-6.45 (m, 1H), 6.50-6.52 (m, 1H), 6.80 (s, 1H), 7.20-7.25 (m, 1H), 7.30 (m, 1H), 7.42 (s, 1H).

Method B.

To a solution of olefin (Intermediate 33 mg, 0.061 mmol) in THF (2 mL) were added NMO (10 mg, 0.079 mmol) and OsO$_4$ solution (0.04 mL, 0.0061 mmol, 4% in water) at room temperature. The reaction mixture was stirred at room temperature for 16 h. The progress of reaction was monitored by TLC. After completion, the reaction mixture was concentrated under reduced pressure and residue purified by reverse phase HPLC to yield the desired compound (19 mg). $^1$H-NMR (400 MHz, CDCl$_3$): δ 7.39 (d, 1H), 6.82 (s, 1H), 6.58 (m, 1H), 6.4 (m, 1H), 4.1 (bs, 1H), 3.9 (s, 3H), 3.72 (t, 2H), 3.6 (m, 1H), 3.45 (m, 1H), 2.18 (s, 2H), 1.23 (m, 2H), 0.8-0.9 (m, 4H). MS: m/z 573.1 [M+H]$^+$.

Example 16

To a solution of olefin (35 mg, 0.065 mmol) in THF (1 mL) were added NMO (10 mg, 0.08 mmol) and OsO$_4$ solution (0.04 mL, 0.0065 mmol, 4% in water) at room temperature. The reaction mixture was stirred at room temperature for 16 h. The progress of reaction was monitored by TLC. After completion, the reaction mixture was concentrated under reduced pressure and residue purified by reverse phase HPLC to yield 5 mg the desired compound. $^1$H-NMR (400 MHz, CDCl$_3$): δ 7.2 (d, 1H), 7.07 (d, 1H), 6.8 (s, 1H), 6.58 (m, 1H), 4.1 (bs, 1H), 3.9 (s, 3H), 3.62 (m, 1H), 3.5 (m, 1H), 3.08 (bs, 1H), 2.4 (m, 1H), 2.0 (m, 2H), 1.62 (d, 2H), 0.79-0.95 (m, 4H). MS: m/z 525 and 527 (1:1) [M+H]+.

Example 17

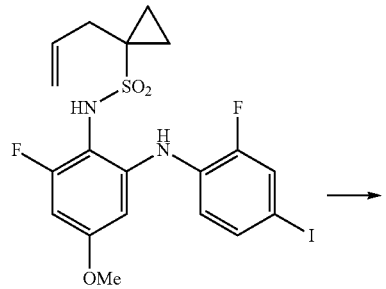

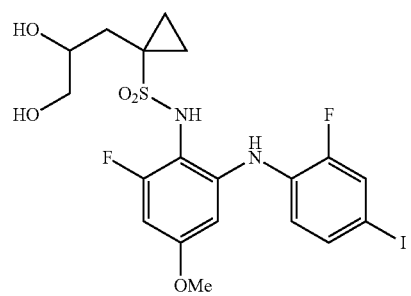

To a solution of olefin (60 mg, 0.11 mmol) in THF (5 mL) were added NMO (18 mg, 0.15 mmol) and OsO4 solution (0.07 mL, 0.011 mmol, 4% in water) at room temperature. The reaction mixture was stirred at room temperature for 16 h. The progress of reaction was monitored by TLC. After completion, the reaction mixture was concentrated under reduced pressure and purified by reverse phase HPLC to yield the desired compound (30 mg). 1H-NMR (400 MHz, CDCl3): δ 7.4 (d, 1H), 7.39 (d, 1H), 7.0 (t, 1H), 6.42 (d, 1H), 6.2 (d, 1H), 4.1 (bs, 1H), 3.82 (s, 3H), 3.75 (t, 1H), 3.62 (m, 1H), 3.5 (m, 1H), 2.5 (bs, 1H), 2.5 (m, 2H), 2.18 (s, 1H), 1.8 (d, 1H), 1.22 (s, 1H), 0.8 (m, 2H). MS: m/z 555.1 [M+H]+.

Example 18

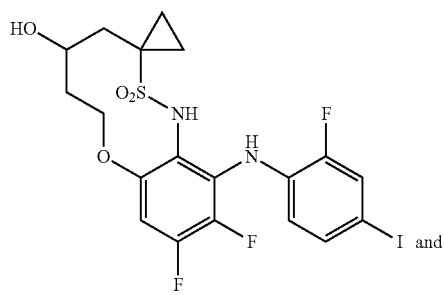

18a and

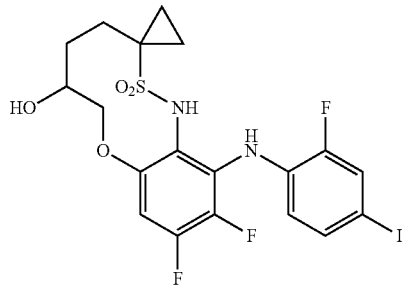

18b

To a solution of metathesis product from Example 1 (100 mg, 0.19 mmol) in dry THF (2 mL) was added BH3-DMS solution (0.3 mL, 0.6 mmol) at room temperature under nitrogen atmosphere. The reaction mixture was stirred at rt for 3 h. The progress of reaction was monitored by TLC. After completion, the reaction mixture was quenched with 2 M aq. NaOH (2 mL). A 30% H2O2 solution (2 mL) was added into the reaction mixture, which was stirred at rt for 30 min, and extracted with ethyl acetate. The organic layer was dried over Na2SO4 and concentrated under reduced pressure. The residue was purified by reverse phase HPLC to yield the isomeric mixture, 18a and 18b (10 mg). 1H-NMR (400 MHz, CDCl3): δ 7.38 (d, 1H), 7.27 (d, 1H), 6.43 (m, 1H), 6.38 (s, 1H), 4.6 (t, 1H), 4.22 (m, 1H), 3.8 (bs, 1H), 3.4 (m, 1H), 2.8 (bs, 1H), 2.42 (m, 1H), 2.0 (m, 2H), 1.5 (bs, 2H), 1.1 (m, 1H), 0.92 (m, 1H), 0.82 (m, 2H). MS: m/z 555.1 [M+H]+.

Example 19

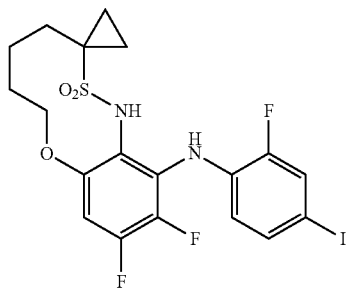 [SMILES: O=S1(=O)Nc2c(cc(F)c(F)c2Nc2ccc(I)cc2F)OCCCCC12CC2]

To a solution of metathesis product prepared in Example 1 (30 mg, 0.056 mmol) in dry THF (1 mL) was added BH3-DMS solution (0.1 mL, 0.2 mmol) at room temperature under nitrogen atmosphere. The reaction mixture was stirred at 50° C. for 16 h. The progress of reaction was monitored by TLC. After completion, reaction mixture was quenched with 2 M aq NaOH (0.6 mL). A 30% H2O2 solution (0.6 mL) was added into the reaction mixture, which was stirred at rt for 30 min, and extracted with ethyl acetate. The organic layer was dried over Na2SO4 and concentrated under reduced pressure. The residue was purified by reverse phase HPLC to yield the desired compound (4 mg). 1H-NMR (400 MHz, CDCl3): δ

7.4 (d, 1H), 7.27 (d, 1H), 6.5 (s, 1H), 6.38 (m, 1H), 3.62 (t, 2H), 1.9 (m, 2H), 1.57 (m, 2H), 1.4 (m, 2H), 1.24 (s, 2H), 1.8 (s, 2H).

Example 20

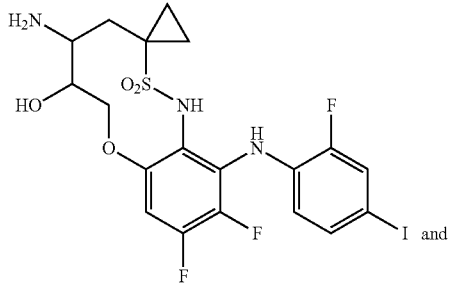

20a

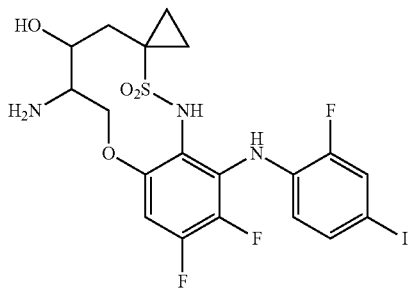

20b

To a stirred suspension of sodium tert-butoxycarbonyl chloroamide (E. Herranz, K, B. Sharpless, *J. Org. Chem.* 1980, 45, 2710-2713) 26 mg, 0.15 mmol) and silver nitrate (27 mg, 0.16 mmol) in acetonitrile (1 mL) were added the metathesis product of Example 1, 53.6 mg, 0.1 mmol) and $OsO_4$ solution (0.01 mL, 0.01 mmol). The reaction mixture was stirred at room temperature for 5 h. The progress of reaction was monitored by TLC. After completion, the reaction mixture was filtered and filtrate concentrated under reduced pressure. The residue was purified by reverse phase HPLC to yield the Boc derivative (10 mg), which was stirred in 30% TFA-DCM solution for 30 min at rt. The reaction mixture was concentrated to yield 7 mg the desired isomeric mixture, 20a and 20b. $^1$H-NMR (400 MHz, $CD_3OD$, TFA): δ 7.42 (d, 1H), 7.38 (d, 1H), 6.8 (m, 1H), 6.5 (m, 1H), 4.5 (d, 2H), 4.05-4.17 (m, 2H), 3.46 (bs, 1H), 3.1 (bs, 1H), 1.97 (d, 2H), 0.81-0.97 (bs, 2H), 0.65 (bs, 2H). MS: m/z 570.3 $[M+H]^+$.

Example 21

N-(3,4-Difluoro-6-methoxy)-2-(2-fluoro-4-iodophenylamino)phenyl-1-(2,3-dihydroxy)cyclopropane-1-sulfonamide

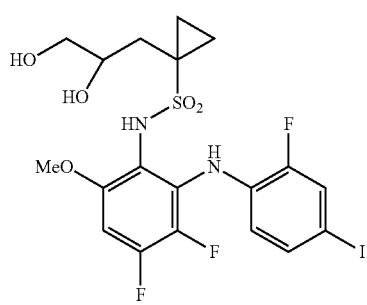 [SMILES: COc1cc(F)c(F)c(Nc2ccc(I)cc2F)c1NS(=O)(=O)C1(CC(O)CO)CC1]

Step 1. Preparation of 3,4,5-trifluoro-2-nitro-phenyl methyl ether

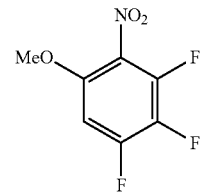

Staring from 3,4,5-trifluoro-2-nitrophenol and dimethyl sulfate in place of allyl bromide and using a procedure analogous to that used to prepare Intermediate 6,3,4,5-trifluoro-2-nitro-phenyl methyl ether was prepared.

Step 2. Preparation of N-(3,4-difluoro-5-methyl-6-nitrophenyl)-2-fluoro-4-iodophenyl)amine Using the procedure analogous to that described for the preparation of Intermediate 7, reaction of 4-iodo-2-fluoroaniline with the product of the previous step provided N-(3,4-difluoro-5-methoxy-6-nitrophenyl)-2-fluoro-4-iodophenyl)amine.

Steps 3 and 4. Preparation of N-(3,4-difluoro-6-methoxy)-2-(2-fluoro-4-iodophenylamino)phenyl-1-(2,3-dihydroxy)cyclopropane-1-sulfonamide Using the procedures analogous to those described above in Steps 4 and 5 of Example 15, the desired compound was obtained. MS analysis: m/z 572 (M+1), $^1$H NMR (400 MHz, $CDCl_3$): 0.86 (m, 2H), 1.21-1.26 (m, 3H), 1.37 (m, 1H), 1.75 (d, 1H), 2.3 (m, 1H), 3.49 (m, 1H), 3.63 (m, 1H) 4.06 (Br s, 1H), 6.43 (m, 1H), 6.53 (m, 1H), 6.87 (s, 1 h), 7.24 (m, 1H), 7.38 (m, 1H).

Example 22

Evaluation for MEK Inhibitory Activity

The compounds were tested using the assays described below.

ERK Example 8 was evaluated for its MEK mediated anticancer activity in various standard in vitro assays as follows In vitro studies of variety of tumor cells lines with prevalent mutations in RAS/RAF genes were performed for anti-proliferative activity (functional assay). This was compared with wild type cell line for selectivity. MEK kinase assay was performed in the presence and in the absence of ATP to define its allosteric inhibitory mode of action; Effect on ERK phosphorylation was studied to establish its cellular mechanism of action.

TABLE 2

Comparisons of In vitro cell survival assays in various cancer cell lines with RAF/RAS mutations

| Cell lines | RDEA 119 (reference) IC$_{50}$(nM) | Example 8 IC$_{50}$(nM) | Mutations expressed |
|---|---|---|---|
| HT29 | 20 | 21 | BRAF |
| Colo205 | 20 | 17 | BRAF |
| HepG2 | 17 | 15 | N-Ras |
| HCT116 | 461 | 544 | K-Ras |
| Caki | >1000 | >1000 | WT |

The IC$_{50}$ values presented are average of two experiments

Compounds of the invention were tested in the HT29 Proliferation cell line and found to have activity; Results for these compounds appear in Table 3.

TABLE 3

| Example No. | HT29 IC$_{50}$<br>a: less than 100 nM<br>b: between 100 and 500 nM<br>c: greater than 500 nm |
|---|---|
| 1 | b |
| 8 | a |
| 8a | a |
| 8b | b |
| 9 | c |
| 10 | b |
| 11 | b |
| 13 | a |
| 15 | b |
| 16 | c |
| 17 | a |
| 18a + 18b | a |
| 19 | c |
| 20a + 20b | a |

MEK Enzyme Inhibitory Assay

Materials and preparation of reagents: Purified recombinant full-length human GST-MEK1 was purchased from Cell Signaling Technology, Inc (Beverly, Mass., USA). MAP kinase substrate Erk1/Erk2 peptide was purchased from Enzo Life Sciences (Plymouth Meeting, Pa., USA).

Determination of enzymatic activity: Compounds were diluted three-fold in dimethylsulfoxide (DMSO) ranging from 1 mM to 1.37 µM concentration. A typical 20-microliter assay contained 80 ng MEK1, 4 µg Erk1/Erk2 peptide, 100 µM or 1 mM ATP, 1 µM to 1.37 nM test compound in 1× assay buffer containing 5 mM MOPS, pH 7.2, 2.5 mM β-glycerophosphate, 1 mM EGTA, 0.4 mM EDTA, 5 mM MgCl$_2$, 0.05 mM DTT. Enzyme reaction was incubated at room temperature for 90 minutes. At the end of kinase reaction, 20 µL of ADP-Glo reagent (Promega, Madison, Wis., USA) was added and incubated at room temperature for 40 minutes. Forty µL of kinase detection reagent (Promega) was added and incubated at room temperature for 1 h. Chemiluminescence was read and IC50s calculated using SoftMax software.

MEK Enzyme Activity Results for the Compound of Example 8: IC$_{50}$=21 Nm

In Vitro Cancer Screen

Colo205, Caki-1, HepG2, HCT116 and HT29 cells were obtained from American Type Culture Collection. Colo205, Caki-1, HepG2 cells were grown in RPMI 1640 medium supplemented with L-glutamine (Invitrogen) and 10% Fetal Bovine Serum (Hyclone) at 37° C. in a humidified, 5% CO$_2$ incubator. HCT116 and HT29 cells were grown in DMEM medium supplemented with L-glutamine (Invitrogen) and 10% Fetal Bovine Serum (Hyclone) at 37° C. in a humidified, 5% CO$_2$ incubator.

Proliferation assay was done by plating 2,000 cells/well in 100 µL of DMEM/10% FBS or RPMI/10% media in a 96-well plate and incubated overnight at 37° C. in a humidified, 5% CO$_2$ incubator. Media was replaced with fresh 100 µL of fresh RPMI/10% FBS media or DMEM/10% FBS media containing various concentrations of the compounds. Compounds were added at 3-fold dilutions, concentrations ranging from 3.3 µM to 4.5 nM. After 72 hour incubation with the compounds at 37° C. in a humidified, 5% CO$_2$ incubator, cell viability was measured in a luminometer after the addition of 100 µL/well CellTiterGlo reagent (Promega). IC50s were calculated using SoftMax software.

Proliferation results for the Compound of Example 8: HT29: 21 nM, Colo205: 17 nM, HepG2: 15 nM, HCT116: 544 nM, Caki-1: >1000 nM The above data indicate the utility of the compounds in treating MEK-modulated diseases in general, and in particular, utility as an anti-tumor agent.

EQUIVALENTS

Although particular embodiments have been disclosed herein in detail, this has been done by way of example for purposes of illustration only, and is not intended to be limiting with respect to the precise form of the disclosed invention or to the scope of the appended claims that follow. In particular, it is contemplated by the inventors that various substitutions, alterations, and modifications may be made to the invention without departing from the spirit and scope of the invention as defined by the claims. Various alterations and modifications of the invention are believed to be a matter of routine for a person of ordinary skill in the art with knowledge of the embodiments described herein. Other aspects, advantages, and modifications considered to be within the scope of the following claims.

What is claimed is:

1. A compound of Formula (I)

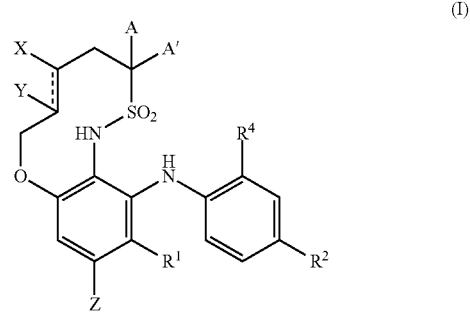

wherein
R$^1$ is H or F;
R$^2$ is Br or I;
R$^4$ is H, F, Cl, or Br;
═══ represents a double or single bond;
X and Y are independently selected from
H,
OH,
OR$^3$, or
NH$_2$,
provided that when ═══ represents a double bond, X and Y are H;
Z is H, F, or OR$^3$;

wherein R³ is C₁-C₆ alkyl; and
A and A' are independently H, or C₁-C₆ alkyl;
or
A and A', together with the C atom to which they are attached, form a cyclopropyl, cyclobutyl or cyclopentyl ring;

or a pharmaceutically acceptable salt, solvate or tautomer thereof.

2. A compound of Formula (Ia)

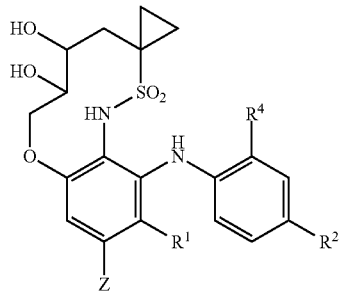

(Ia)

wherein
R¹ is H or F;
R² is Br or I;
R⁴ is H, F, Cl, or Br;
and
Z is H, F, OR³, wherein R³ is C₁-C₆ alkyl;

or a pharmaceutically acceptable salt, solvate, or tautomer thereof.

3. A compound of claim 2 wherein
R¹ is H or F;
R² is Br or I;
R⁴ is H, F, Cl, or Br, and
Z is H, F, or OMe;

or a pharmaceutically acceptable salt, solvate or tautomer thereof.

4. A compound of Formula (Ic):

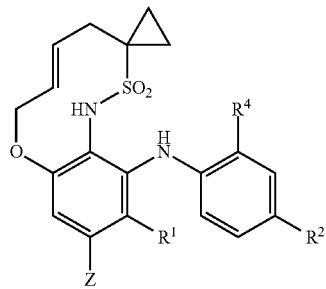

(Ic)

wherein
R¹ is H or F;
R² is Br or I;
R⁴ is H, F, Cl, or Br;
Z is H, F, or R³, or a pharmaceutically acceptable salt, solvate or tautomer thereof.

5. A compound selected from

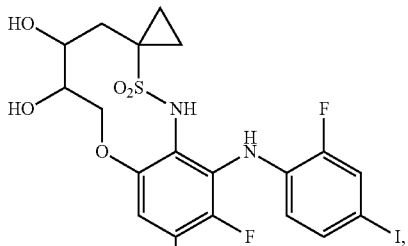

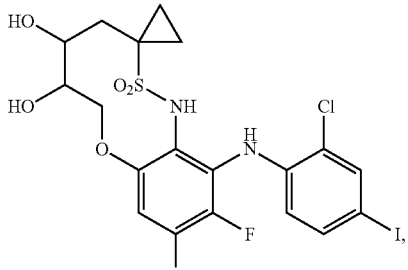

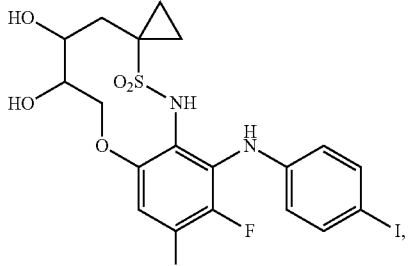

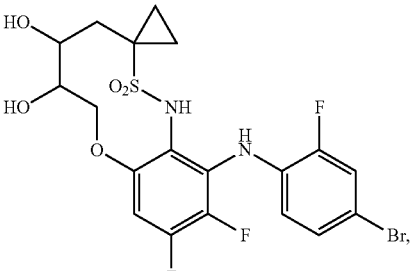

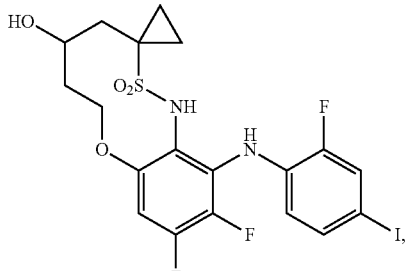

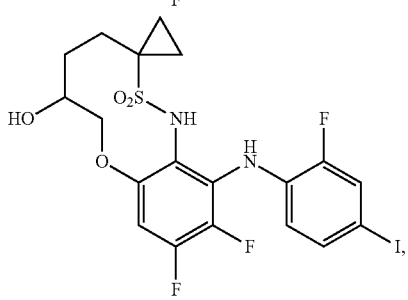

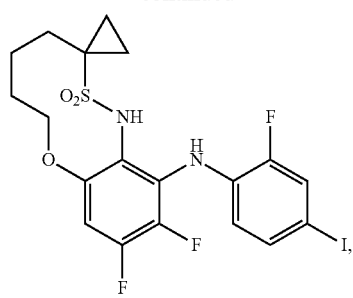
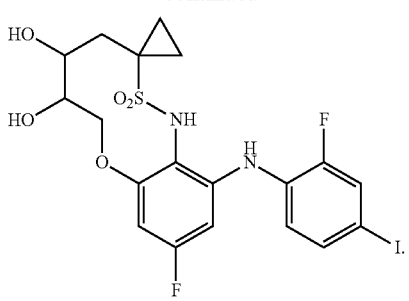
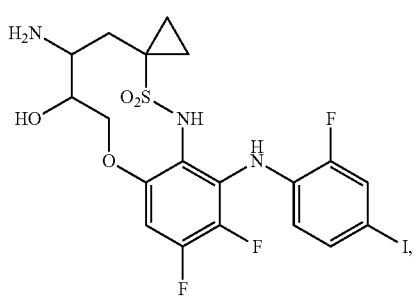
6. A compound selected from
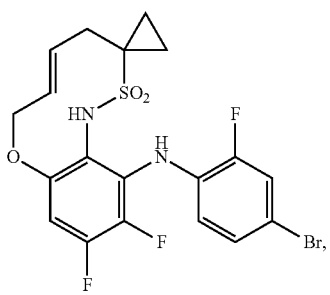
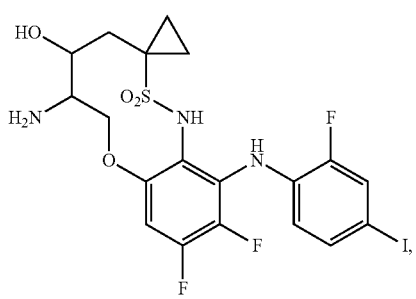
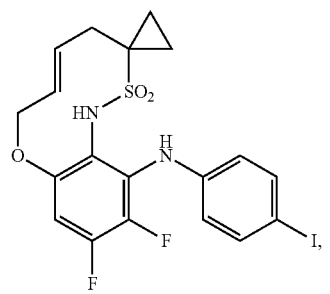
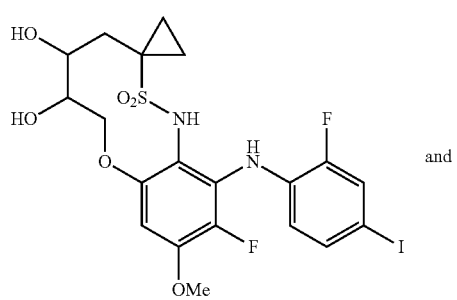
and -continued

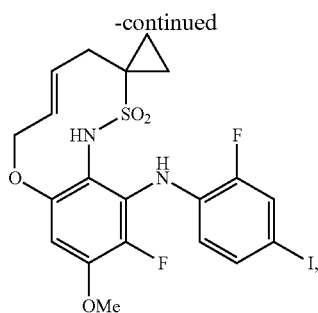

-continued

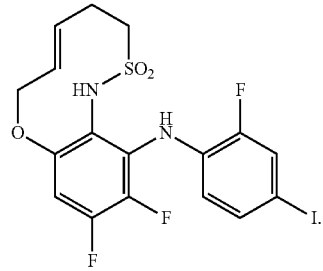 [SMILES: O=S1(=O)CC/C=C/COc2cc(F)c(F)c(Nc3ccc(I)cc3F)c2N1]

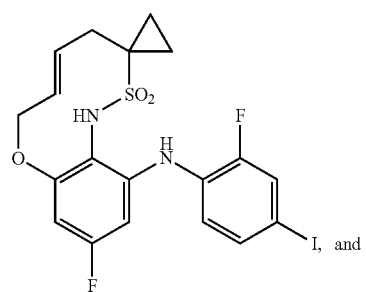

7. A method of treating arthritis in a mammal, comprising administering to said mammal a therapeutically effective amount of the compound of Formula (I), or a pharmaceutically acceptable salt, solvate, or tautomer thereof.

8. A method of treating cancer, comprising administering to a subject in need thereof an effective amount of a compound of Formula (I), wherein the cancer is selected from the group consisting of colon cancer, liver cancer, melanoma, and non-small cell lung cancer.

9. A pharmaceutical composition comprising an effective amount of a compound of Formula (I) or a pharmaceutically acceptable salt, solvate, or tautomer thereof.

10. A method of inhibiting a MEK enzyme, comprising contacting the enzyme with an effective inhibitory amount of a compound of Formula (I).

* * * * *